United States Patent [19]
Sarrine et al.

[11] Patent Number: 4,827,780
[45] Date of Patent: May 9, 1989

[54] AUTOMATIC PIPETTING APPARATUS

[75] Inventors: Robert J. Sarrine, Beaumont; Henry A. Garsee, Kountze, both of Tex.

[73] Assignee: Helena Laboratories Corporation, Beaumont, Tex.

[21] Appl. No.: 89,025

[22] Filed: Aug. 24, 1987

Related U.S. Application Data

[63] Continuation of Ser. No. 853,201, Apr. 17, 1986, abandoned.

[51] Int. Cl.$^4$ .............................................. B01L 3/02
[52] U.S. Cl. ............................. 73/864.21; 204/299 R; 422/102; 422/70; 210/198.3
[58] Field of Search ........... 73/863.31, 863.32, 863.01, 73/863.33, 864.21; 204/299 R, 182.7, 182.8, 182.9; 422/102, 62, 69, 70, 55, 100, 56, 68.02, 68.08, 63, 67; 436/169; 210/198.3, 658; 435/815

[56] References Cited

U.S. PATENT DOCUMENTS

| | | | |
|---|---|---|---|
| 3,266,554 | 8/1966 | Brownrigg | 210/198.3 |
| 3,536,449 | 10/1970 | Astle | 73/863.32 |
| 3,585,129 | 6/1971 | Delfel | 210/198.3 |
| 3,616,387 | 10/1971 | Siebert et al. | 204/299 R |
| 3,902,852 | 9/1975 | Lemieux et al. | 73/863.32 |
| 3,915,856 | 10/1975 | Meyer | 210/198.3 |
| 4,004,548 | 1/1977 | Smola et al. | 210/198.3 |
| 4,166,766 | 9/1979 | Metzenberg et al. | 435/815 |
| 4,264,327 | 4/1981 | Blum | 422/82 |
| 4,272,381 | 6/1981 | Kremer et al. | 422/70 |
| 4,375,401 | 3/1983 | Catsimpoolas | 204/299 R |
| 4,478,094 | 10/1984 | Salomaa et al. | 73/863.32 |
| 4,494,403 | 1/1985 | Bowers et al. | 73/863.58 |
| 4,503,011 | 3/1985 | Hubeau | 422/102 |
| 4,554,839 | 11/1985 | Hewett et al. | 73/863.32 |
| 4,578,169 | 3/1986 | Vicario et al. | 204/182.7 |

FOREIGN PATENT DOCUMENTS 0097655 6/1983 Japan .................................. 422/70

Primary Examiner—Stewart J. Levy
Assistant Examiner—Robert R. Raevis
Attorney, Agent, or Firm—Dodge, Bush & Moseley

[57] ABSTRACT

An automatic pipetting apparatus is disclosed having a base on which is mounted a vertical frame supporting a row of positive displacement pipettes which are driven in the up or down direction by an electromechanical mechanism under microprocessor controls. The apparatus includes a base, a track and a carriage longitudinally movable beneath the row of pipettes. The carriage includes an independent translating and position signal generation mechanism. The carriage carries a tray which includes sample chambers, a space to receive a microporous electrophoresis support medium, such as a cellulose acetate strip, a wash well, rinse well and a space to receive blotting paper. The pipettes include a barrel and a plunger capable of aspirating and dispensing from 0.5 to 5 $\mu$l of liquid. The barrels move up and down with respect to the base by means of another independent translating and signal generating mechanism. The barrels may be easily replaced from the mechanism if they become damaged or worn from many operating cycles. The apparatus under microprocessor program control, washes, rinses, blots the barrels before and after each application or engagement of the barrels with a liquid or contaminant.

32 Claims, 10 Drawing Sheets

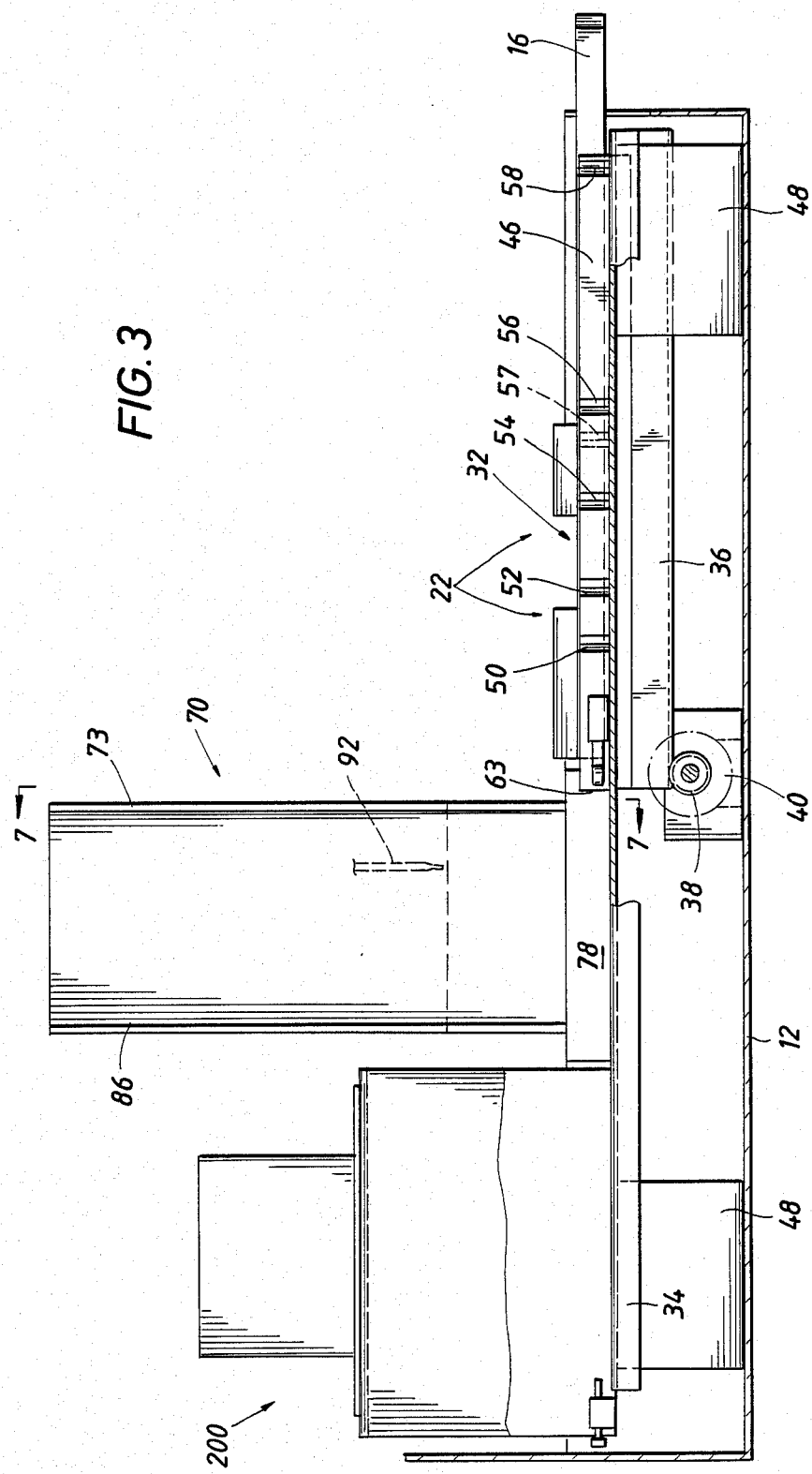

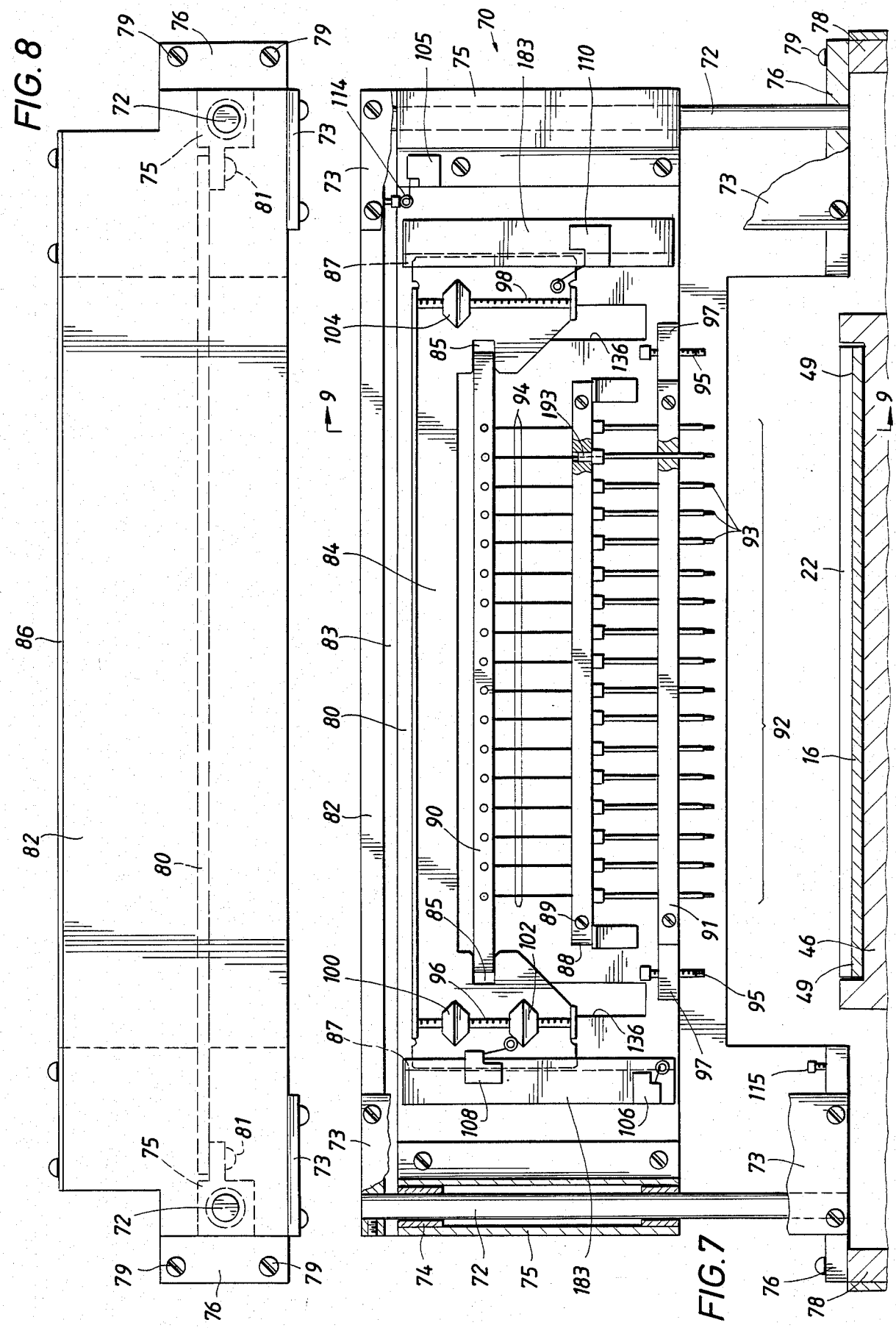

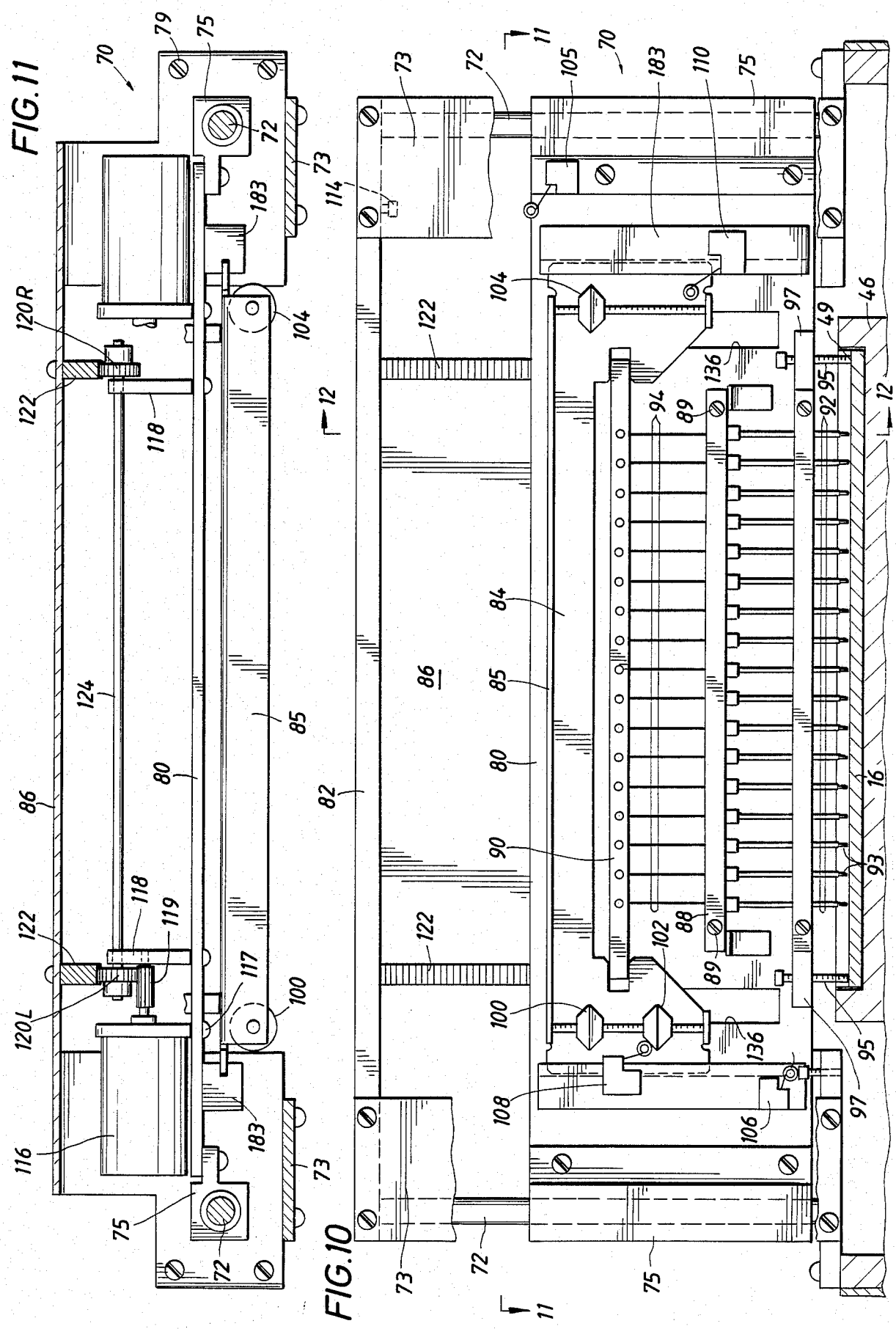

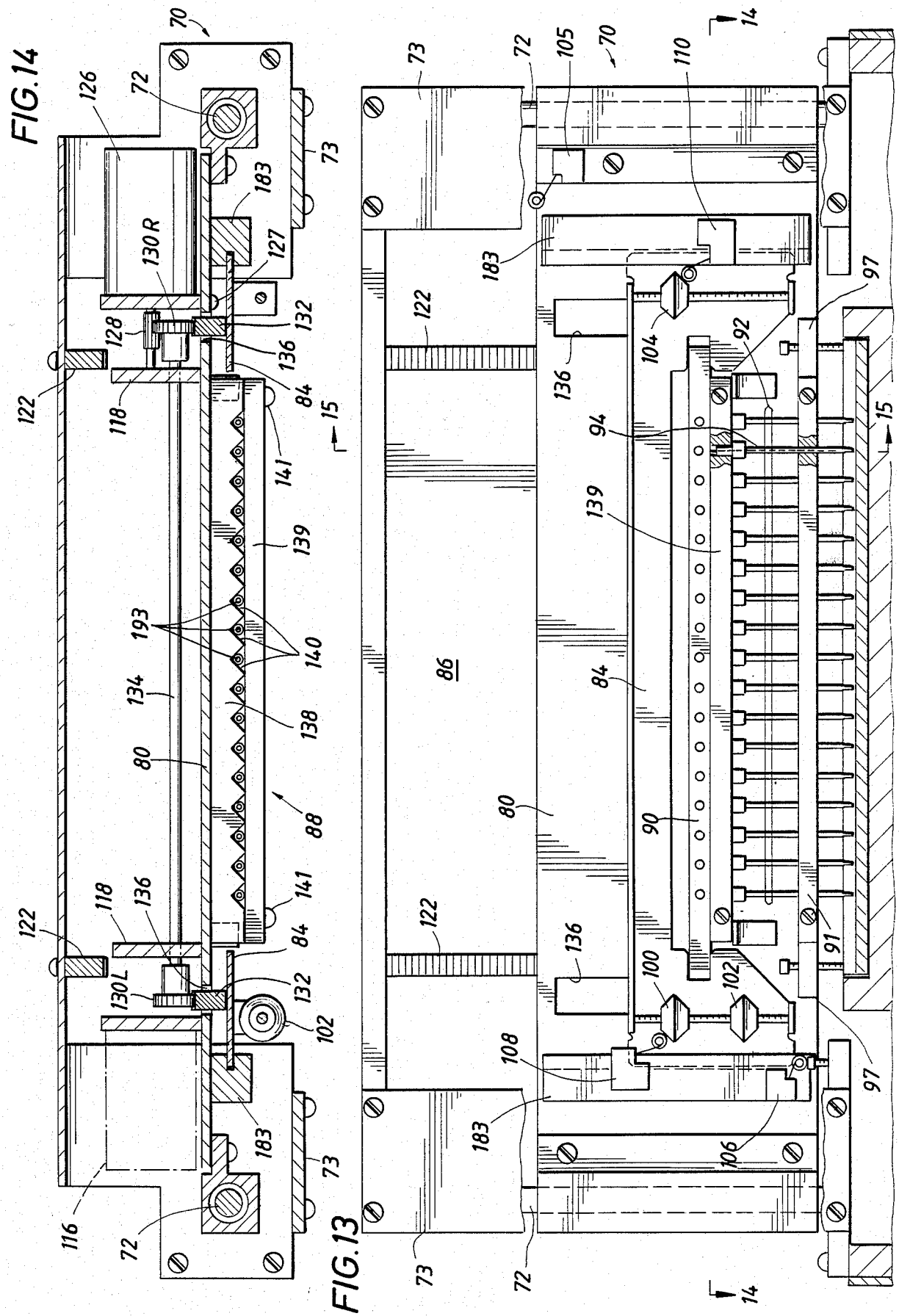

ical signals representative of the relative longitudinal
AUTOMATIC PIPETTING APPARATUS This application is a continuation of application Ser. No. 853,201, filed Apr. 17, 1986, now abandoned.

BACKGROUND OF THE INVENTION

1. Field of the Invention

This invention is related in general to the field of applying fluid samples to analysis strips. In particular, this invention relates to an automatic pipetting apparatus for applying multiple fluid samples to a microporous support medium such as a cellulose acetate or agarose strip which may be used in the field of zone electrophoresis and with other separation techniques including the field of thin layer chromatography. Zone electrophoresis is the science of moving charged particles in an electric field through a solid or semi-solid medium. The technique is most commonly used in medical research and medical laboratories for analyzing various blood proteins.

2. Description of the Prior Art

In the electrophoresis technique, a blood or other fluid sample is applied to a support medium which is then subjected to an electric field so as to separate the components of the sample. The support media used in the electrophoresis process includes cellulose acetate, agar, agarose and acrylamide gels. In laboratory work it is desirable that a plurality of samples be applied to the support medium such that each of the samples may be subjected to the electric field at the same time.

The samples may be applied to the support medium one at a time in serial fashion with a hand pipetter, but the hand pipetter must be rinsed with a cleansing agent and blotted before a new sample is aspirated and then applied to the strip.

Applicators have been designed to apply fluid samples simultaneously or in "parallel" to the strips. Such applicators are described at page 61 of the General Products Catalog for 1984-1985 of Helena Laboratories with offices in Beaumont, Tex. Such applicators may apply eight, twelve or more samples to a microporous support medium and have the advantage of making the electrophoresis technique easier and more reproducible.

The applicators known prior to this invention however have been essentially non-automatic applicators and required cleaning of the applicator tips after each application to the support medium.

Automatic dispensing systems are known in the prior art. For example, a system sold under the trademark "Well Washers" of BioTech Instruments, Inc. of Burlington, Vt. provides an alignment mechanism by which a row of eight or twelve barrels may be positioned above one of a plurality of rows of washing vials or wells. Automation in the system provides selection of dispensing fill volumes, soaking times and number of wash cycles.

None of the prior art however has provided an apparatus for automatically filling a plurality of pipetters from a respective plurality of fluid chambers and then precisely applying such fluid samples from each pipette to a support medium. Another disadvantage of the prior art systems is that there has been no means for automatically washing and cleaning the barrels during each cycle time so as to prevent contamination of each of the barrels during application of a new plurality of fluid samples to a new support medium.

Another disadvantage of the prior art is that there has been no means for precisely automatically applying a very small amount—of the order of one micro liter of sample liquid—to a support medium.

Another disadvantage of the priot art is that there has been no means for precisely automatically diluting a very small amount—of the order of one micro liter—of sample fluid with a diluting liquid, and precisely applying a very small amount of the diluted sample to a support medium.

IDENTIFICATION OF OBJECTS OF THE INVENTION

It is therefore a primary object of the invention to provide an automatic pipetter apparatus for aspirating from a plurality of sample chamber wells into a corresponding plurality of pipetters and then applying such samples precisely to a microporous support medium to be used in electrophoresis or thin layer chromatography.

It is a further object of the invention to provide an automatic pipetting apparatus which not only aspirates and dispenses sample fluids onto a support medium strip such as cellulose acetate or agarose, but also flushes, cleanses, rinses and blots the tips of the barrels with an appropriate cleaning fluid before and after each application of the sample fluid to the support medium.

It is another object of the invention to provide an automatic pipetting apparatus by which positive displacement pipette barrels and plungers are controlled to precisely apply a very small sample of fluid to a support medium.

It is another object of the invention to provide automatic pipetting apparatus for precisely automatically diluting a very small amount of sample fluid with a diluting liquid and precisely applying a very small amount of the diluted sample to the support medium.

SUMMARY OF THE INVENTION

The objects identified above as well as other advantages and features of the invention are provided in an automatic pipetting apparatus which generally includes a base and a sample plate disposed on the base and a pipette frame including a vertical support for supporting the frame from the base above the sample plate. The sample plate includes a row of individual liquid sample chambers and a lateral application space longitudinally separated from the liquid chamber row. The lateral application space is adapted to receive a microporous support medium. A mounting plate is carried by the pipette frame.

The apparatus includes translation means for effecting relative longitudinal movement of the pipette frame and sample plate, and vertical translation means for effecting relative vertical movement of the mounting plate and the sample plate.

A plurality of microsyringe barrels are removably secured to the mounting plate. The barrels are spaced corresponding to the spacing of the liquid chambers of the sample plate. A plurality of micro-plungers are provided, one each movably disposed in one of the barrels. A plunger translation means is provided for moving the plunger vertically within the barrels.

Signalling means are provided for generating longitudinal signals representative of the relative longitudinal orientation of the pipette frame with respect to the sample plate, for generating mounting plate signals representative of the vertical orientation of the mounting plate relative to the sample plate and for generating plunger signals representative of the orientation of the plungers relative to the barrels.

A programmed digital computer is provided responsive to the longitudinal signals, the mounting plate signals and to the plunger signals for generating a sequence of control signals to the longitudinal translation means, to the vertical translation means and to the plunger translation means to aspirate a predetermined amount of liquid from the sample chambers into the respective pipette barrels, and to apply the liquid samples in the barrels onto corresponding spaces or "spots" on the microporous support medium when placed on the lateral application space of the sample plate.

One embodiment of the invention includes a base having a track disposed longitudinally on it. A carriage is longitudinally movably disposed on the track [means] and carries a sample plate which is removably disposed on the carriage. The carriage plate includes a lateral row of individual liquid sample chambers and a lateral application space which is longitudinally separated from the liquid chamber row. The lateral application space is adapted to receive a microporous support medium such as a cellulose acetate or agarose strip used in electrophoresis or thin layer chromatography.

A pipette assembly is mounted vertically on the base above the carriage and the sample plate. The pipette assembly includes vertical mounting posts separated laterally from each other and secured to the base. A mounting plate assembly is slidably guided by the posts and is disposed laterally with respect to the sample plate.

The mounting plate assembly includes a mounting plate having slidable guides disposed about the posts. A pipette bar is fixed to the mounting plate. A plurality of microsyringe barrels are provided in a row on the pipette bar with their heads secured thereto. The microsyringe barrels are spaced corresponding to the spacing of the liquid chambers on the plate. The barrels are hollow, each barrel having a lower tip.

A plunger bar is vertically movably disposed above the tip bar and has a plurality of micro-plungers secured thereto. Each of the micro-plungers are movably disposed within a corresponding barrel of the microsyringes. A plunger actuator plate carried by the mounting plate is vertically movable with respect to the mounting plate. The actuator plate is removably secured to the plunger bar.

Translation and signalling means are provided for moving the carriage longitudinally forward and backward beneath the mounting plate assembly and generating carriage position signals indicative of the carriage position. A translation and signalling means is provided for moving the mounting plate assembly up and down with respect to the base and generating mounting plate position signals indicative of the mounting plate position. A translation and signalling means for moving the plunger bar up and down with respect to the mounting plate and generating plunger bar position signals indicative of the plunger bar position is provided.

A programmed microcomputer is provided responsive to the carriage position signals, to the mounting plate position signals, and to the plunger bar position signals for generating a sequence of control signals to the translation means for moving the carriage, the translation means for moving the mounting plate, and the translation means for moving the plunger bar so as to aspirate a first predetermined amount of liquid from the sample chamber into the respective pipette barrels and then to apply the liquid in each of the pipette barrels onto corresponding spaces of the support medium when placed on the lateral application space of the sample plate.

The sample plate includes a wash well and waste well longitudinally spaced form each other and from the sample chamber. The programmed computer generates a further sequence of control signals to the translation means before aspirating liquid from the sample chambers to draw a second predetermined amount of rinse liquid from the wash well into the respective pipette barrels and then to discharge that rinse liquid into the waste well.

The apparatus further provides the sample plate with a longitudinal blotting space for applying a lateral blotting paper strip where the blotting space is longitudinally separated from the sample chamber row, the wash well, the waste well and the lateral application space. The programmed computer generates a further sequence of control signals to the translation means after discharging the wash liquid into the waste well so as to blot the lower tips of the barrel on the blotting paper strip.

Preferably, the sample plate includes a raised portion and a lower portion where the row of individual liquid sample chambers and the wash well and the waste well are disposed on the raised portion and the lateral application space and the blotting space are disposed on the lower portion.

The sample plate may include a row of liquid dilution wells longitudinally spaced from the sample chambers. The programmed computer includes a program, actuated by a dilution signal, for automatically controlling the apparatus for diluting the samples aspirated to the microsyringe barrels with dilution fluid and mixing the sample and dilution fluid in each of the dilution wells before mixed diluted sample fluid is applied to the spots of the support medium.

BRIEF DESCRIPTION OF THE DRAWINGS

The objects, advantages and features of the invention will become more apparent by reference to the drawings which are appended hereto and wherein like numerals indicate like parts and wherein an illustrative embodiment of the invention is shown, of which:

FIG. 3 is a side view partially cut away and in section with the cover removed and taken from the view along lines 3—3 of FIG. 1;

FIG. 4 is a cross-section of the carriage and the sample plate;

FIG. 7 is a forward looking view taken along lines 7—7 of FIG. 3 and shows partially broken away, partially cross-sectional parts of the pipette assembly slidably mounted on posts secured to the base and including a mounting plate which moves up and down with respect to the base and carrying a row of barrels of individual pipettes and an actuator plate movable vertically with respect to the mounting plate for moving a plunger bar vertically for moving individual plungers within the barrels of each of the pipettes;

FIG. 8 shows a top view of the pipette assembly showing in dashed lines the mounting plate of the pipette assembly;

FIG. 10 is a similar view to that of FIG. 7 but shows the mounting plate having been translated to a lower position but with the plunger bar remaining in an upward position whereby the tips of the pipetters are in a downward position, but the plungers are extended upwardly from each of the barrels of the pipettes;

FIG. 11 is a top cross-sectional view taken along lines 11—11 of FIG. 10 and illustrates the motor and rack and pinion system by which the mounting plate is moved up and down with respect to the base;

FIG. 13 is a view similar to that of FIGS. 7 and 10 but illustrates the plunger actuator plate and plunger bar moved downwardly with respect to the mounting plate thereby forcing the plungers associated with each of the pipetters into their barrels and forcing any fluid previously aspirated into the barrels out the tips of the barrels;

FIG. 14 shows a cross-sectional view taken along lines 14—14 of FIG. 13 and illustrates the rack and pinion system by which the actuator plate and the plunger bar secured thereto is moved up and down with respect to the mounting plate;

DESCRIPTION OF THE INVENTION

Figure 1:
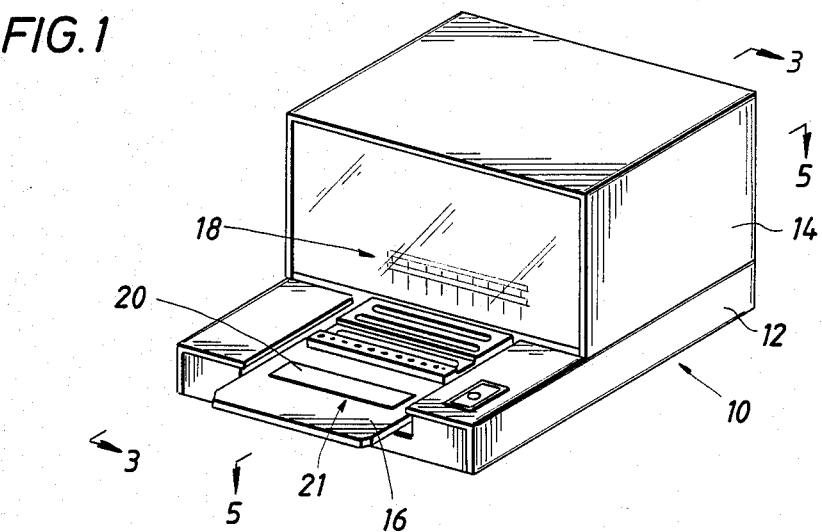
FIG. 1 shows a perspective view of one embodiment of the automatic pipetting apparatus of the invention with a sample plate secured thereto and its cover attached.

FIG. 1 illustrates in a perspective view the automatic pipetting apparatus 10 according to the invention. The apparatus includes a base 12 on which a sample plate 16 is movably supported. The sample plate includes a space 21 for securing a microporous support medium 20 such as a cellulose acetate or agarose strip used in the field of zone electrophoresis or other separation techniques including the field of thin layer chromatography. A cover 14 is provided behind which a pipette head 18 is shown.

Figure 2:
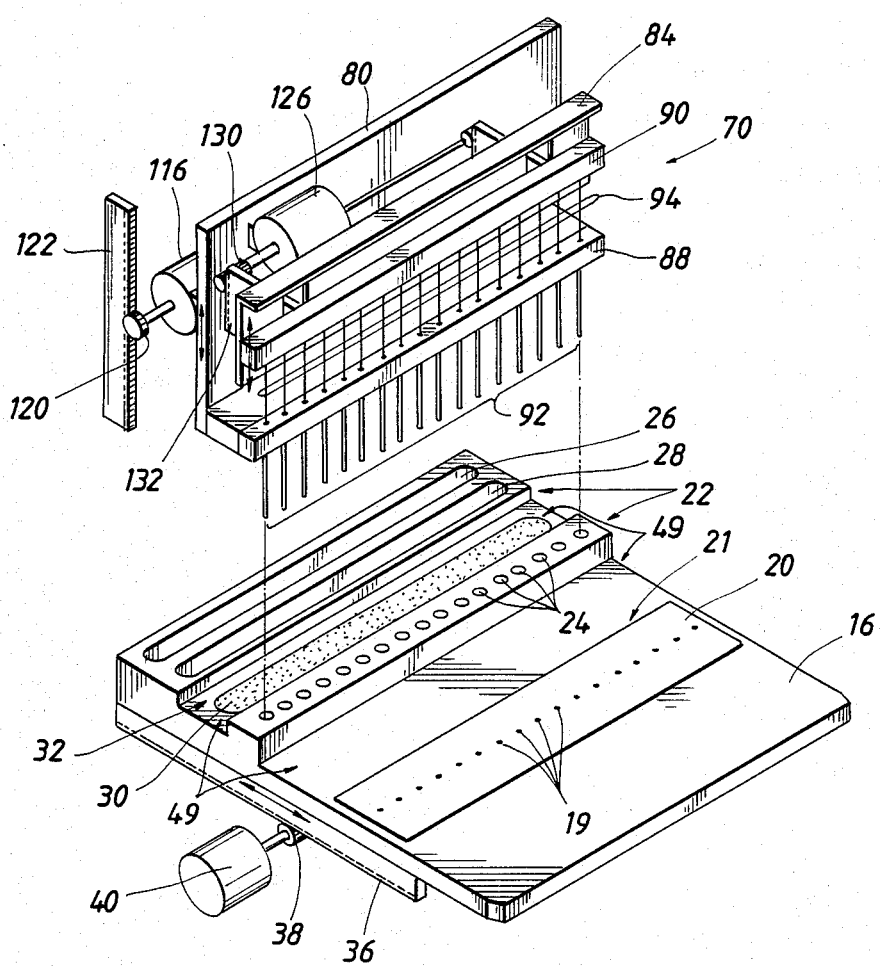
FIG. 2 is a schematic illustration of the invention showing the functional relationship between the sample plate with its sample chambers, wash well, waste well and a longitudinal application space with a microporous support medium secured thereto beneath a pipette assembly in which individual pipette barrels are moved as a unit up and down and a plunger bar secured to plungers which are moved up and down with respect to the barrels.

FIG. 2 is a schematic illustration of the essential mechanical elements of one embodiment of the invention with the base and the cover removed. None of the mounting apparatus is shown in FIG. 2 so as to simplify the explanation of the relationship of the sample plate 16 to the pipette assembly 70. The translational means are shown in a functional way rather than in actual mechanical detail which will be shown in detail in the figures and discussion below.

The sample plate 16 as shown includes a row of sample chambers 24 as well as a wash well 26, rinse or "waste" well 28 and a longitudinal space 21 on which a microporous support medium 20 is removably secured. The sample chambers 24, the rinse well 28 and the wash well 26 are provided on raised portions 22 of the sample plate. If desired, a plastic cup may be provided in each of sample chambers 24. A blotter space 32 between the rinse well 28 and the sample chambers 24 is provided at substantially the same vertical level 49 as the sample application space 21 on which the support medium 20 is secured.

As illustrated in FIG. 2, the various regions of the sample plate are longitudinally distinct, yet the lateral spacings between the sample chambers 24 corresponds to the application spots 19 on the support medium 20 which is indicative of the fact that the barrels 92 of the pipette assembly 70 are arranged in a row corresponding to the sample chambers 24. Liquid from those chambers is aspirated by the automatic pipetting apparatus and is applied in a similar row on the spots 19 of the microporous support medium 20.

It is advantageous to provide the sample chambers 24, waste well 28 and wash well 26 in raised portions 22 of the sample plate 16 so that the mounting plate 80 of the pipette assembly 70 need only go down to a common downward position during all wash, waste, blot, sampling and application operations. However, it would be obvious to one of ordinary skill in the art that other arrangements could be provided especially where different levels of the mounting plate could be provided in the translation and signalling apparatus for controlling the mounting plate 80. A detailed discussion of such translation and signalling apparatus for controlling the mounting plate 80 is discussed below.

The schematic illustration of FIG. 2 shows that the sample plate 16 is translated in forward and rearward directions beneath the pipette assembly 70 by virtue of the motor 40 turning a pinion 38 having its gears in engagement with those of rack 36. As the shaft of the motor 40 turns, the sample plate 16 carried by the rack 36 moves back and forth beneath the pipette assembly 70.

Turning now to the pipette assembly 70 shown in FIG. 2, a mounting plate 80 is translated upwardly and downwardly by means of mounting plate motor 116 having its pinion 120 engaging a rack 122. Thus, the entire mounting plate 80, and the microsyringe barrels 92 attached to the barrel bar 88 which is secured to the mounting plate 80, moves up and down in accordance with the turning of the mounting plate motor 116. Similarly, the plungers 94 which are attached to plunger bar 90 and actuator plate 84 are moved up and down with respect to mounting plate 80 by operation of the turning of actuating plate motor 126 and its pinion 130 engaging actuator rack 132. For purposes of illustration, the actuator plate motor 126, its pinion 130 and the actuator plate rack 132 are shown on the forward side of mounting plate 80, but the actual apparatus illustrated in the subsequent figures is to the rearward side of the mounting plate 80 through slots in it.

FIG. 2 therefore shows all of the essential elements as far as the translation of the sample plate 16 backward and forward beneath the microsyringe barrels 92 and illustrates the upward and downward translation means of the mounting plate 80 and the microsyringe barrels 92, and the upward and downward motion of the plungers 94 and the plunger bar 90 and actuator plate 84 with respect to the mounting plate 80.

Figure 2A:
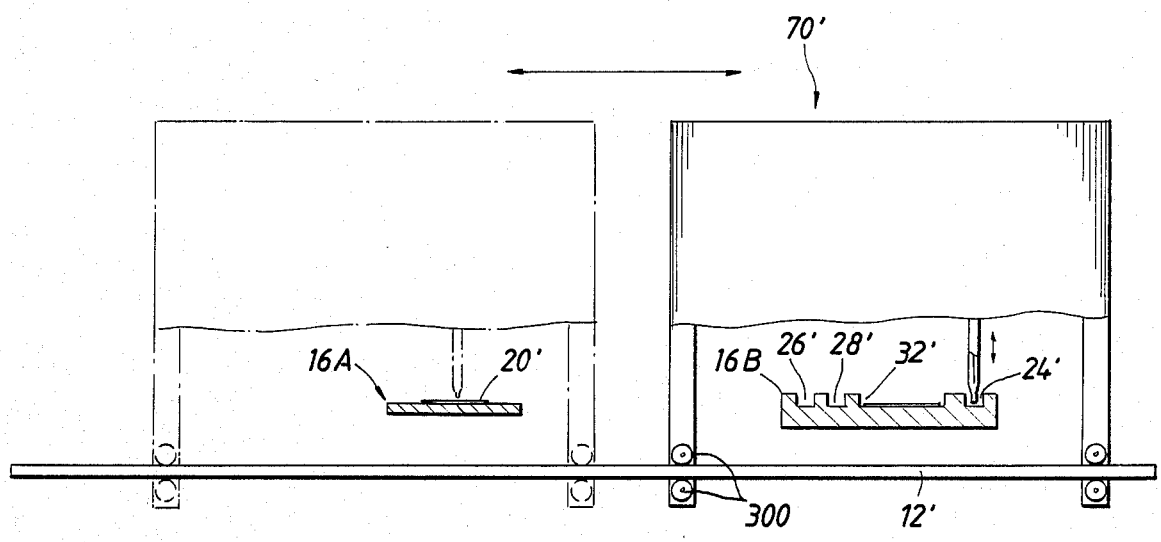
FIG. 2A schematically shows another embodiment of the invention where the mounting plate includes two stationary units and the pipette frame is longitudinally movable with respect to the plate.

FIG. 2A schematically illustrates an alternative embodiment of the invention where the sample plate remains immovable with respect to the base 12' with the pipette assembly 70' being mounted on rollers 300 for longitudinal translation. FIG. 2A illustrates that the sample plate may include two units, an application plate unit 16A and a fluid plate unit 16B. The sample plate unit 16A is adapted to removably secure a support medium 20', while the fluid plate unit 16B includes a row of sample chambers 24', a waste well 28', a wash well 26' and a blotting space 32'. The operation of the alternative embodiment is similar to that of the embodiment of FIG. 2 except that translation and signalling means are provided for longitudinally translating pipette assembly 70' with respect to the sample plate(s) 16A, 16B. Details of such translation and signalling means will be apparent to one of ordinary skill in this art by virtue of the detailed description of analagous translation and signalling means described below.

Figure 2B:
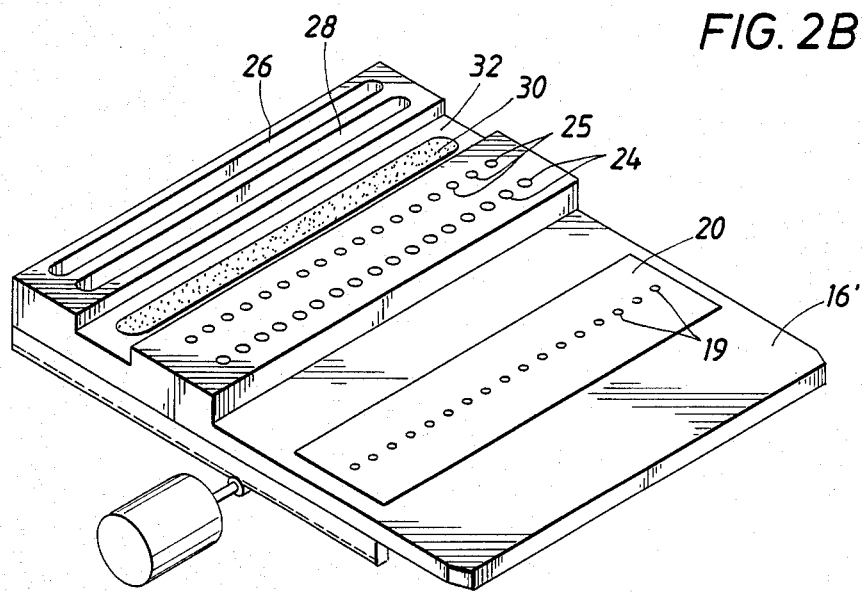
FIG. 2B is a perspective view of another embodiment of the sample plate further including a row of dilution wells.

FIG. 2B illustrates an alternative sample plate 16' which may include an additional row of dilution wells 25 in addition to the row of sample chambers 24, waste well 28, wash well 26 and blotting space 32. Explanation of the automatic diluting of sample fluid will be described below with reference to FIG. 2B.

FIG. 3 is a side view taken along lines 3—3 of FIG. 1 with a portion of track 34 cut away to show its construction. The tracks 34 are supported by track supports 48 which may also be seen in FIG. 5. The pipette assembly 70 is vertically supported from base mounting block 78 which is secured to the sides of the base 12 and is also further illustrated in FIG. 5. The pipette assembly 70 includes a back plate 86 and a front plate 73. One of the plurality of barrels 92 of the pipette assembly is shown in an upward position.

Figure 6:
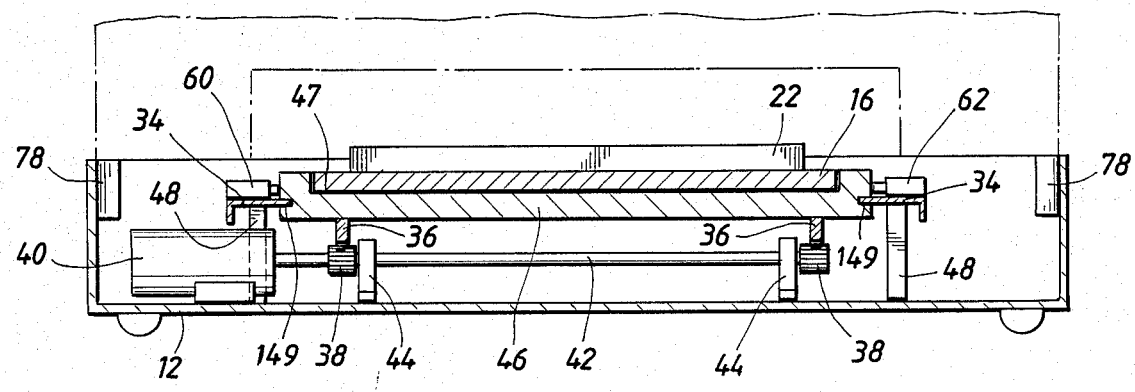
FIG. 6 is a cross-sectional view taken along lines 6—6 of FIG. 5 and shows the base, the carriage and sample plate according to the invention and further shows the translation and guiding means by which the track is moved forward and backward with respect to the pipetting assembly.

A carriage 46 is slidably movably disposed on track 34 as more clearly seen in FIG. 6. Racks 36 are secured to carriage 46 and are movable with respect to the base 12 by means of the carriage motor 40 having its pinion 38 in engagement with rack gear 36.

Notches are provided along the left edge of the carriage 46. These notches cooperate with a trip switch to provide signals indicative of the longitudinal position of the carriage. The wash notch 50, rinse notch 52, blot notch 54, sample chamber notch 56, dilution chamber notch 57 (where the alternative sample plate 16' of FIG. 2B is used) and application notch 58 are illustrated in FIG. 3.

FIG. 4 illustrates a vertical cross-section through the carriage 46 and the plate 16 and shows the actual wash well 26, rinse well 28 and one of the sample chambers 24 on raised portion 22 of the plate 16. A blotter space 32 and a lateral application space 21 are illustrated on plate 16. Blotter paper 30 is shown in blotter space 32 while a microporous support medium 20 such as cellulose acetate or agarose is secured in lateral application space 21.

Figure 5:
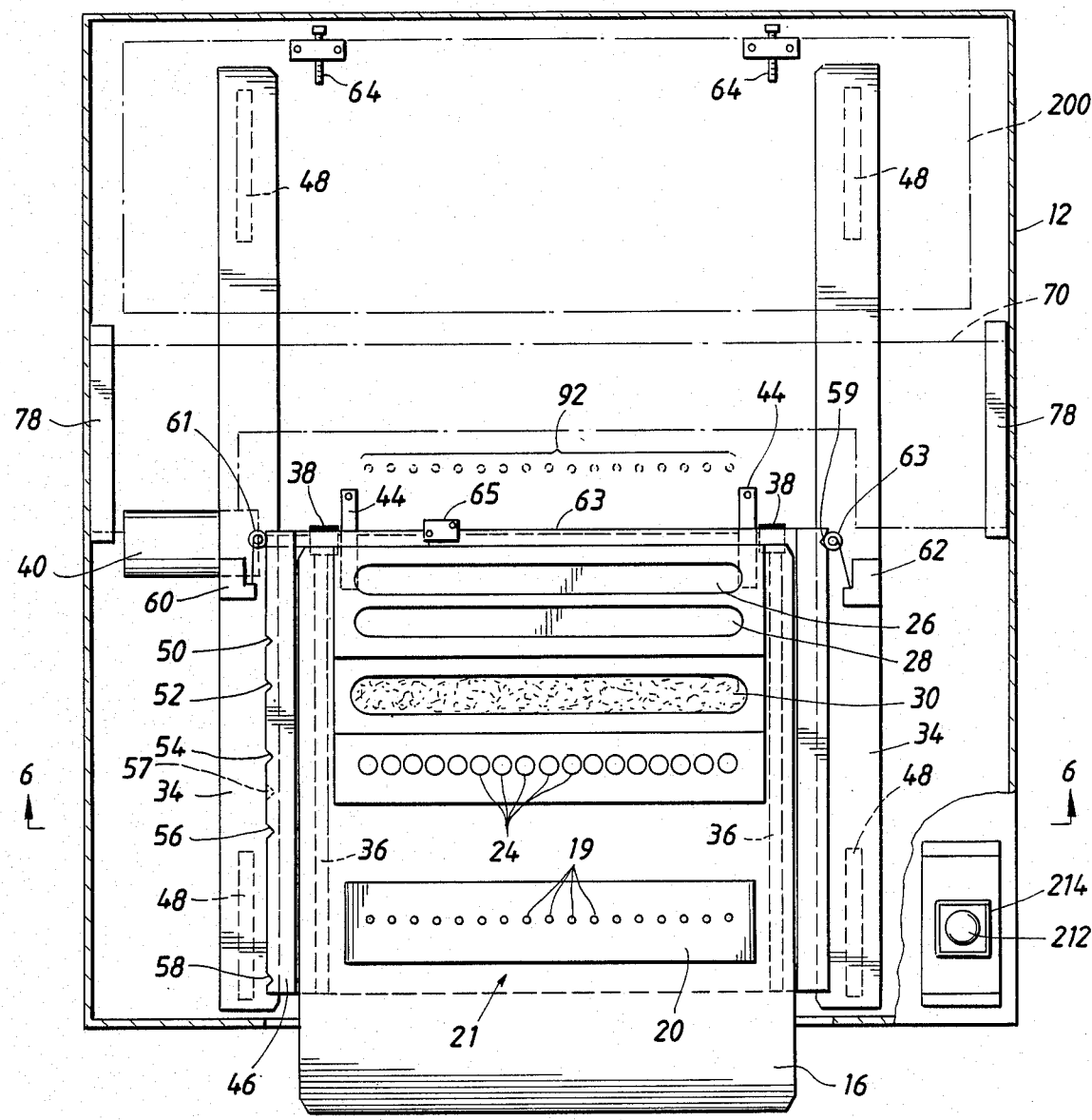
FIG. 5 is a downward looking view along lines 5—5 of FIG. 1 and shows the cross-section of the base at level 5—5 and the track, carriage and sample plates beneath the pipetting assembly.

FIG. 5 is a downward view taken along lines 5—5 of FIG. 1. Carriage 46 is shown supported by tracks 34 and movable in the rearward and forward directions by means of motor 40, pinion 38 and rack 36 as also illustrated in FIG. 6. The sample plate 16 is disposed in a valley or U-shaped cross-sectional structure 47 of carriage 46.

Position signalling notches on the sides of the carriage 46 cooperate with trip switch 60 and trip switch 62 fixed to tracks 34. Spring loaded rollers 61 and 63, respectively are forced against the longitudinal edges of carriage 46 and into the notches as the carriage 46 moves past them. For example, the notches on the left hand side 46 include the wash notch 50, the waste notch 52, the blot notch 54, the sample chamber notch 56 and an application notch 58. The notches correspond to the longitudinal position of the wash well 26, waste well 28, blotter paper 30, sample chambers 24 and application spots 19 when those wells, chambers and blotting and application spots are directly beneath the pipette barrels 92.

When the carriage 46 moves rearwardly where the wash well 26 is directly beneath the barrels 92, the roller 61 moves into the wash notch 50 thereby tripping the trip switch 60 for signalling the microprocessor associated with electronic module 200 (FIGS. 3 and 16) that the wash well is beneath the barrels 92. The trip switch 60 is likewise tripped when the roller 61 enters notches 52, 54, 56 and 58 to signal the position of the respective other wells, chambers and spots beneath the barrels 92.

On the right hand side of the carriage 46 is notch 59 in which the roller 63 is shown. A sample plate trip swtich 62 is thereby tripped to indicate that the carriage is at its maximum forward position. Trip switch 65 is mounted on the rear edge of carriage 46. Switch 65 closes when the rear edge of the plate 16 is in position and engages it thereby generating a signal that the plate 16 is properly in position on carriage 46. The stops 64 provide means for accurately longitudinally positioning application spots 19 beneath barrels 92 when carriage 46 is in the maximum rearward position.

Also shown in FIG. 5 is a start button 214 by which the programmed microprocessor is signalled to start the automatic sequence of events for the automatic pipetting apparatus which will be explained in detail below. Lamp 212 provides a visual indication to the user of the automatic pipetting apparatus 10 that the power is turned on.

FIG. 6 illustrates in a cross-sectional view taken along lines 6—6 of FIG. 5 the means by which the carriage is translated with respect to tracks 34. The tracks 34 are supported upon base 12 by means of supports 48. The carriage 46 includes slots 149 in its sides on which it slides on tracks 34.

Plate 16 as indicated above is disposed within a notch or valley 47 of the carriage 46. The carriage translation motor 40 is fixed to the base 12 and includes a shaft 42 which is supported by means of shaft supports 44. Pinions 38 secured to shaft 42 have their gears in engagement with racks 36 which are attached to the carriage 46. As the motor 40 is turned in one direction or the other under control of the microprocessor in the electronic module 200 (FIG. 16), the carriage 46 moves in the forward or rearward directions.

FIG. 7 illustrates the pipette assembly 70 looking rearwardly along lines 7—7 of FIG. 3. The mounting blocks 76 are shown secured to the base mounting blocks 78 by means of screws 79. The mounting blocks 76 carry vertical mounting posts 72 as illustrated in FIGS. 7, 10 and 13 and in the top views of FIGS. 8, 11 and 14. The front plates 73 and back plate 86 are secured by means of screws to mounting blocks 76.

A mounting plate 80 is vertically slidably supported about the vertical mounting posts 72. Retainer bearings 74 provide sliding engagement between the posts 72 and vertical bearing blocks 75. The mounting plate 80 is fastened to extensions of bearing blocks 75 by means of screws 81. By reference to FIGS. 7 and 13, it is seen that mounting plate 80 may be moved from its upward position as shown in FIG. 7 to its lower position as shown in FIG. 13 by its attachment to bearing blocks 75 and their sliding engagement on posts 72.

A barrel bar 88 is secured to mounting plate 80 by means of screws 89. Mounted on barrel bar 88 are a plurality of pipette barrels 92 having their heads 193 secured within the barrel bar 88 in a manner to be described below. As illustrated in the partial cut away of barrel bar 88, the barrel lock bar 91 secures the lower portions of the barrels 92 to provide stability to the barrels. Guide tips 97 include adjustable screws 95 extending below the bottom edge of the mounting plate 80 which cooperate with the lower surfaces 49 of plate 16 to accurately vertically position the lower tips 93 of barrels 92 with respect to the support medium 20 and blotting paper 30 disposed on lower surface 49 of plate 16. Such adjustment allows the droplets which form on the ends of the tips 93, when plungers 94 are driven downwardly within barrels 92, to "kiss" or be slightly applied either to the support medium or the blotting paper. The droplets on the lower tips 93 of the barrels 92 are held because of their small size (as small as one micro liter) and surface tension forces of the barrel tips. When the tips are brought to a small distance within the upper surface of the support medium 20 or blotting paper 30, the droplets are relieved of the surface tension holding them to their barrels and are precisely applied to the blotting paper or to the support medium.

Acutator guides 183 are secured to the mounting plate 80 and include grooves in which an actuator plate 84 is inserted for sliding movement upwardly and downwardly with respect to the mounting plate 80. The actuator plate 84 has grooves in which a plunger bar 90 is inserted. The plungers 94 of the microsyringe barrels 92 are secured to the plunger bar 90 and extend within the barrels 92. As illustrated in FIG. 7, the plungers 94 are at their uppermost extent with respect to the barrels 92. The actuator plate 84 is adapted to move downwardly with respect to the mounting plate 80, and through such action, the plunger bar 90 moves downwardly with respect to the barrel bar 88 causing plungers 94 to move downwardly within the barrels 92 thereby forcing any fluid within such barrels outwardly through the tips 93 of the barrels and forming a droplet at the tips of the barrels.

Position signals are generated indicative of the position of the mounting plate 80 with respect to the base 12 and the position of the actuator plate 84 and its plungers 94 with respect to the mounting plate 80. The trip switch 106 mounted on the mounting plate 80 cooperates with the lower stop 115 mounted on the mounting block 76 to provide a lower mounting plate position signal when the mounting plate 80 reaches its lower extent. In a similar way as shown on the right hand side of the mounting plate 80, the upper trip switch 105 is mounted on the mounting plate 80 and is shown tripped by contact with the upper stop 114. The upper trip switch 105 when tripped provides a signal to the microprocessor of electronics module 200 (FIG. 3) indicative that the mounting plate 80 is in its upper position.

The trip switch 108 mounted on left hand side actuator 183 cooperates with application position cam 100 and wash cam 102. The trip switch 108 is tripped by the application cam 100 when the actuator plate 84 moves upwardly with respect to the mounting plate 80 and the trip switch 108 is tripped by wash cam 102 as the actuator plate 84 moves further upwardly. The down cam 104 trips trip switch 110 mounted on the right hand side actuator guide 183 when the actuator plate 84 reaches its maximum downward travel where the plungers 94 are within the barrels 92.

Figures 9, 12, 15:
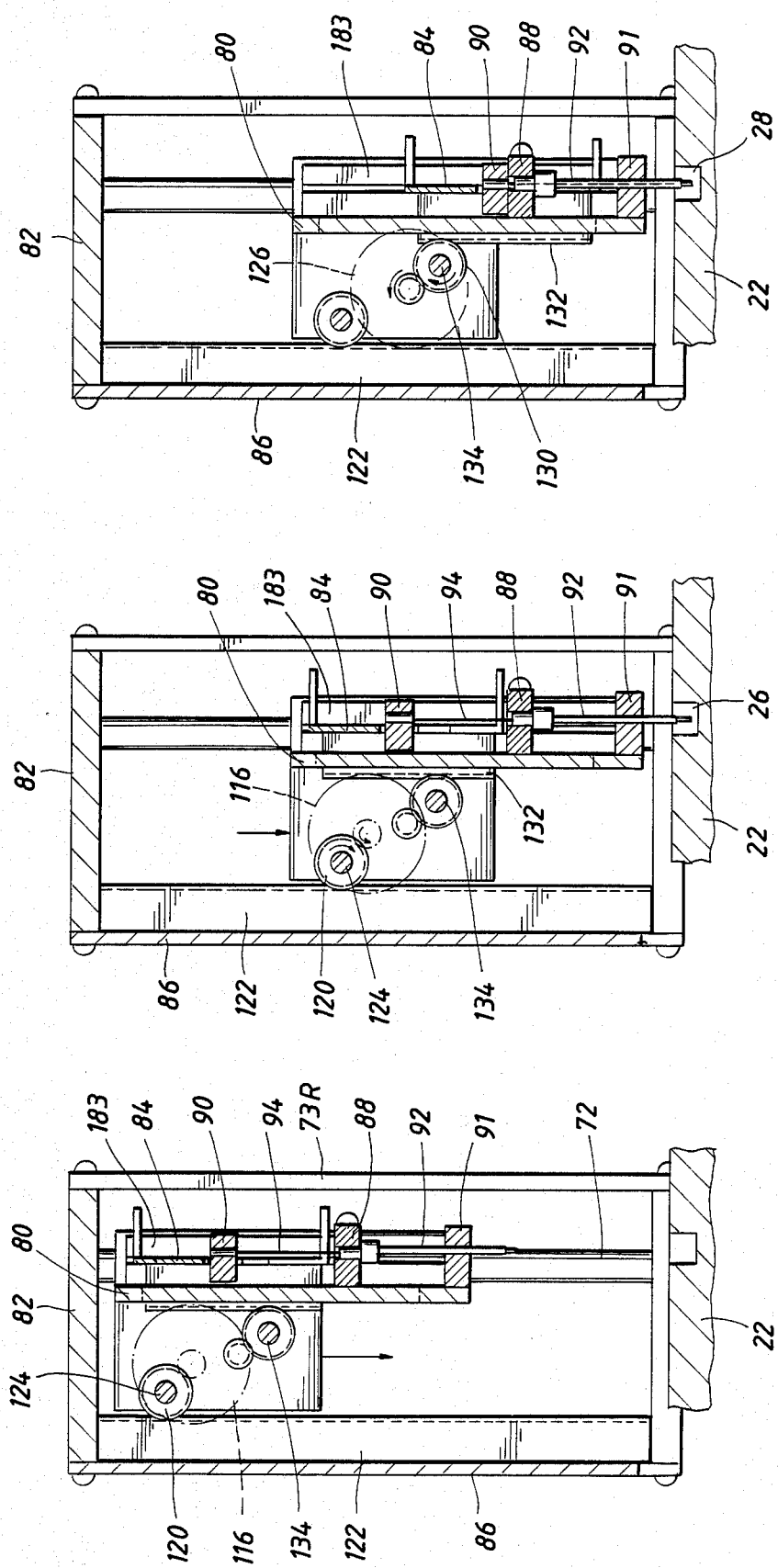
FIG. 9 shows a cross-sectional view taken along lines 9—9 of FIG. 7 and illustrates the relationship between the mounting plate, the tip bar and the plunger bar and the means by which the mounting plate is moved up and down with respect to the base.
FIG. 12 is a cross-sectional view taken along lines 12—12 of FIG. 10 and illustrates the relationship of the mounting bar after it has been moved downwardly by the rack and pinion system by operation of the motor turning with respect to the frame mounted rack.
FIG. 15 is a cross-sectional view taken along lines 15—15 of FIG. 13 and illustrates the movement of the actuator plate downwardly with respect to the mounting plate by operation of the rack and pinion system controlling relative movement between the actuator plate and the mounting plate.

FIG. 9 is a cross-sectional view taken along lines 9—9 of FIG. 7 and illustrates the mounting plate 80 and the actuator plate 84 both in their upward positions. Mounting plate motor 116 has driven the mounting plate 80 to the upward position by operation of pinion 120 on rack 122 which is secured to the back plate 86 and to the base of the apparatus.

Turning now to FIG. 10, the pipette assembly 70 is shown with the mounting plate 80 in the downward position but the plunger bar 90 and the plungers 94 are in their upward position with respect to the barrel bar 88. The barrels 92 are in a downward position in the wash well for aspirating 5 µl fluid, for example, from the wash well 26.

FIG. 11, a view of the pipette assembly looking downwardly along lines 11—11 from FIG. 10, illustrates the drive mechanism by which the mounting plate 80 is moved up and down with respect to the base. A mounting plate actuator motor 116 is fixed to the mounting plate 80 by means of a mounting screw 117. The output shaft of the motor 116 has a gear 119 fixed to it. Gear 119 is engaged with a left pinion gear 120L which is mechanically coupled to a right pinion gear 120R by means of shaft 124. The shaft is mounted to the mounting plate 80 by shaft mountings 118. Racks 122, fixed to the back plate 86, have their gears in engagement with pinion gears 120L and 120R. As the motor 116 turns in either direction under microprocessor control, the mounting plate 80 is moved upwardly or downwardly with respect to the base and the back plate 86 by the rack and pinion mechanism. The front view (FIG. 10) of the pipette assembly 70 with the mounting plate 80 in a downward position shows the racks 122 visible. The front view also illustrates, with the mounting plate 80 in its maximum downward position, that stop screws 95 of guide tips 97 are slightly above surfaces 49 of the plate 16 indicative that tips 93 are slightly above the top edge 49 of the plate so that droplets which form on the tips may "kiss" the surface 49 and apply sample fluid to the support medium or blotting paper.

FIG. 12 is a cross-sectional view of the pipette apparatus taken along lines 12—12 of FIG. 10 and shows that the mounting plate actuator motor 116 has turned its pinion gear 120 so that the mounting plate 80 has been moved downwardly with respect to the base and the raised portion 22 of the plate 16. Thus, the barrel 92 has been lowered to be within a well of the raised portion 22 of the sample plate. A wash well 26 is illustrated as an example where the barrels 92 of the pipettes have been lowered by the mounting plate 80 and where the fluid from the wash wells have been aspirated into barrels 92 by virtue of the plungers 94 being pulled upwardly by means of the actuator plate 84. It is apparent from FIGS. 11 and 12 that the mounting plate 80 is translated upwardly and downwardly with respect to the raised portion 22 by means of the motor 116 turning and causing the pinion 120 to translate upwardly and downwardly on fixed rack 122.

Turning now to FIG. 13, the state of the pipette apparatus 70 is such that the actuator plate 84 has moved downwardly causing the plungers 94 to be inserted back into the barrels 92 thereby positively displacing any fluid which has been aspirated within the barrels either to an application space, a blotter, or to a waste well. It is seen that the trip switch 108 has been returned to a condition such that any upward movement of the actuator plate 84 will be tripped first by the application cam 100 and then the wash cam 102 providing a means for signalling the position of the actuator plate 84 with respect to the mounting plate 80.

FIG. 14, is a downward looking view along lines 14—14 of FIG. 13 and illustrates the drive mechanism by which the actuator plate 84 is translated upwardly and downwardly with respect to the mounting plate 80. A plunger bar actuator plate motor 126 is fixed to the mounting plate 80 by means of a mounting screw 127. The motor 126 includes a gear 128 on its output shaft which is in engagement with pinion gear 130R. Pinion gear 130R is coupled to a pinion gear 130L by means of a shaft 134 which is supported by means of shaft mountings 118 which also supports shaft 124 (see FIG. 11). The actuator plate 84 has actuator plate racks 132 fixed to the rear side thereof which extend through slots 136 in the mounting plate so as to engage the pinions 130L and 130R. As the plunger bar actuator plate motor 126 is caused to turn in either the clockwise or the counterclockwise direction, the actuator plate 84 is caused to move upwardly or downwardly with respect to the mounting plate 80. FIG. 13 shows the slots 136 in the mounting plate 80 through which the actuator plate racks 132 extend.

FIG. 14 also shows the means by which the barrel heads 193 of the barrels 92 are removably fixed to the barrel bar 88. The barrel bar 88 comprises a receiving bar 138 having slots 140 provided along its front face. The barrel heads 193 are inserted therein and secured by means of a securing bar 139 which holds the barrels vertically in place. The securing bar 139 is secured to the receiving bar 138 by means of screws 141. The barrel lock bar 91 similarly constructed as the barrel bar 88. The barrel bar 88 provide a removably securing means by which the barrels 92 may be easily replaced due to wear or breakage.

FIG. 15 is a cross-sectional view looking along lines 15—15 of FIG. 13 and illustrates the mounting plate 80 in a downward position. The actuator plate 84 has been translated downwardly where the plunger bar 90 is adjacent the barrel bar 88. FIG. 15 illustrates the actuator plate racks 132 extending through slots of the mounting plate 80 and their engagement with pinion gear 130 which has been turned by means of the actuator plate motor 126. The barrel 92 is now in a rinse well 28, for example. The plunger 94 has been forced down by means of the actuator plate 84 moving the plunger bar 90 to its lowermost position. Of course, the raised portion of the plate 22 has moved longitudinally with respect to the pipette assembly between the views of FIGS. 12 and 15.

Figure 16:
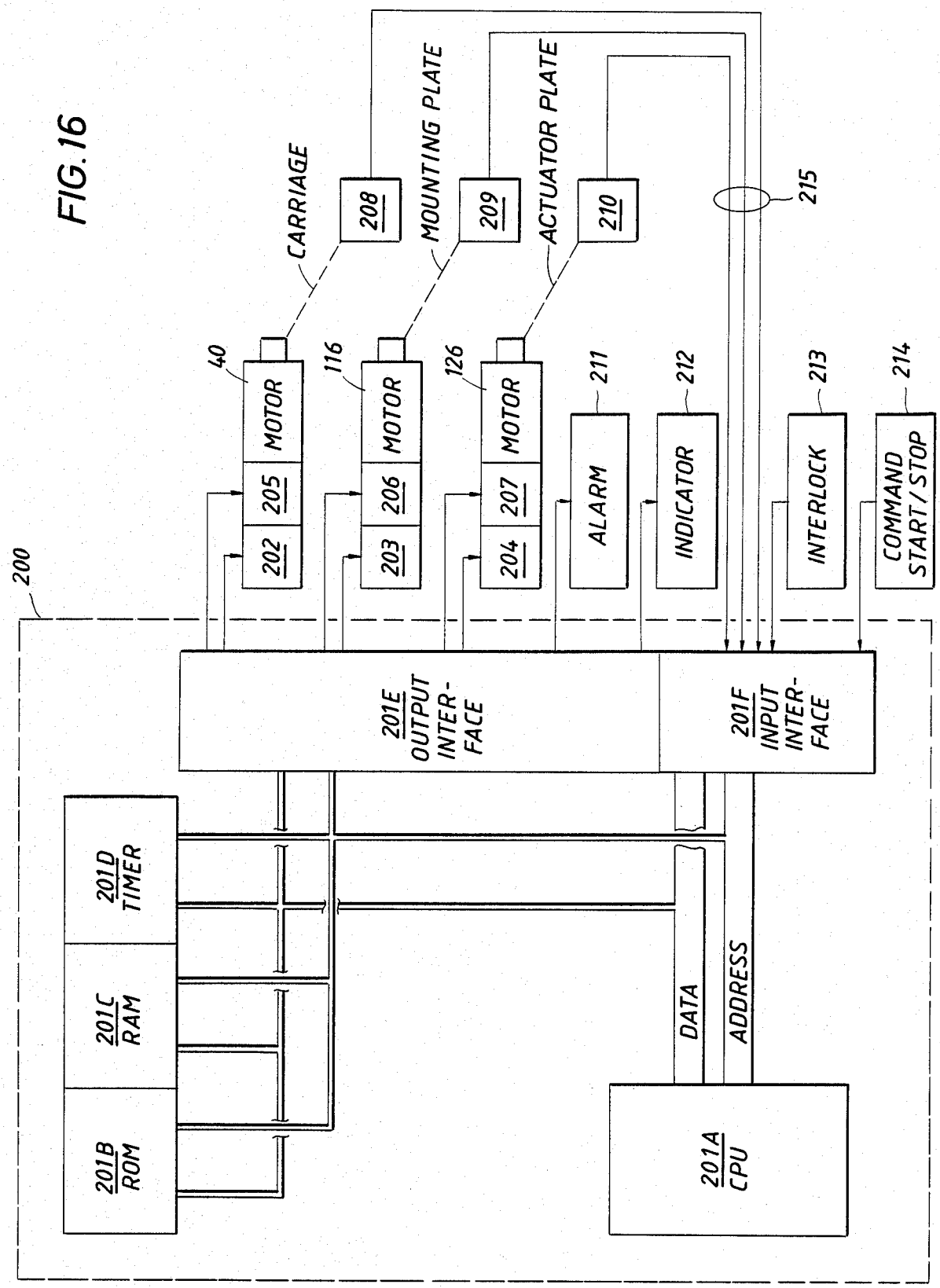
FIG. 16 is a schematic illustration of the microcomputer integrated circuit device receiving signals from position detector circuits associated with the carriage, the mounting plate and actuator plate and applying translation signals to motors for positioning the carriage, the mounting plate and the plunger actuator plate.

FIG. 16 illustrates schematically the means by which the carriage mounting plate and plunger actuator bars are controlled to perform the automatic pipetting operation.

The dotted box 200 represents a microcomputer integrated circuit device, preferably a microcircuit No. HD68P01V07 manufactured by the Hitachi Corporation. The circuit includes a central processing unit 201A, a read only memory 201B, a random access memory 201C, a timer 201C, a timer 201D, an output interface circuit 201E and input interface circit 201F. The read only memory circuit 201B includes stored software by which the entire automatic operation is controlled and will be discussed below.

FIG. 16 illustrates the carriage motor 40, the mounting plate 116 and the actuating plate motor 126 all under computer control via the motor driver circuits 202, 203, 204 such as circuits UDN-2952B manufactured by the Sprague Corporation. These motor driver circuits are used to control the speed of the motor and its direction of rotation. Also provided in conjunction with the motor are electronic break circuits 205, 206, 207 which are provided to quickly break the motor's rotation on receipt of a translation signal by the computer 200. Such electronic motor break circuits are preferably 2N6075 Triac circuits.

The position detector circuits 208 represent the circuitry with the trip switches 60 and 62 illustrated in FIG. 5 which indicate the position of the carriage 46 and the sample plate 16 with respect to the pipette assembly.

The position detector circuits 209 represent the circuitry associated with the lower trip switch 106 and the upper trip switch 105 which signal the upward or downward limits of travel of the mounting plate 80 with respect to the base.

The position detector circuits 210 represent the circuitry associated with trip switches 108 and 110 which indicate the relative position of the actuator plate 84 with respect to the mounting plate 80. The signals associated with each of those position detector circuits are represented as being carried by a bundle of electrical leads 215 to the input interface circuitry 201F of electronic module 200.

The alarm circuit 211 is provided for the apparatus, for example, such as a sounding device EAF14R06C manufactured by Panasonic. Such circuit is activated and a sound is generated to signal faults in the operation of the apparatus or to signal the readiness of the machine.

Indicator circuit 212 represents an indicator lamp as illustrated in FIG. 5 to signal the user that the power is on to the apparatus. The interlock circuit 213 represents the circuitry with sample plate interlock trip switch 65 which indicated the presence or absence of the sample plate on the carriage. Command circuit 214 represents a push button switch used to start or abort the automatic pipetting application process.

In operation, the central processing unit 201A receives the sequences of events instructions from the programs stored in the read only memory 201B. The central processing unit 201A then receives positional information concerning the moving mechanisms of the apparatus by means of reading and decoding the binary coded data present at the input interface 201F which receives information via leads 215 from the position detector circuits 208, 209, 210.

The microprocessor CPU 201A then receives an input command to start or abort the process by means of reading and decoding the binary coded data present at the input interface 201F which is connected to the command circuit 214 which may be the push button 214 illustrated in FIG. 5.

Figure 17:
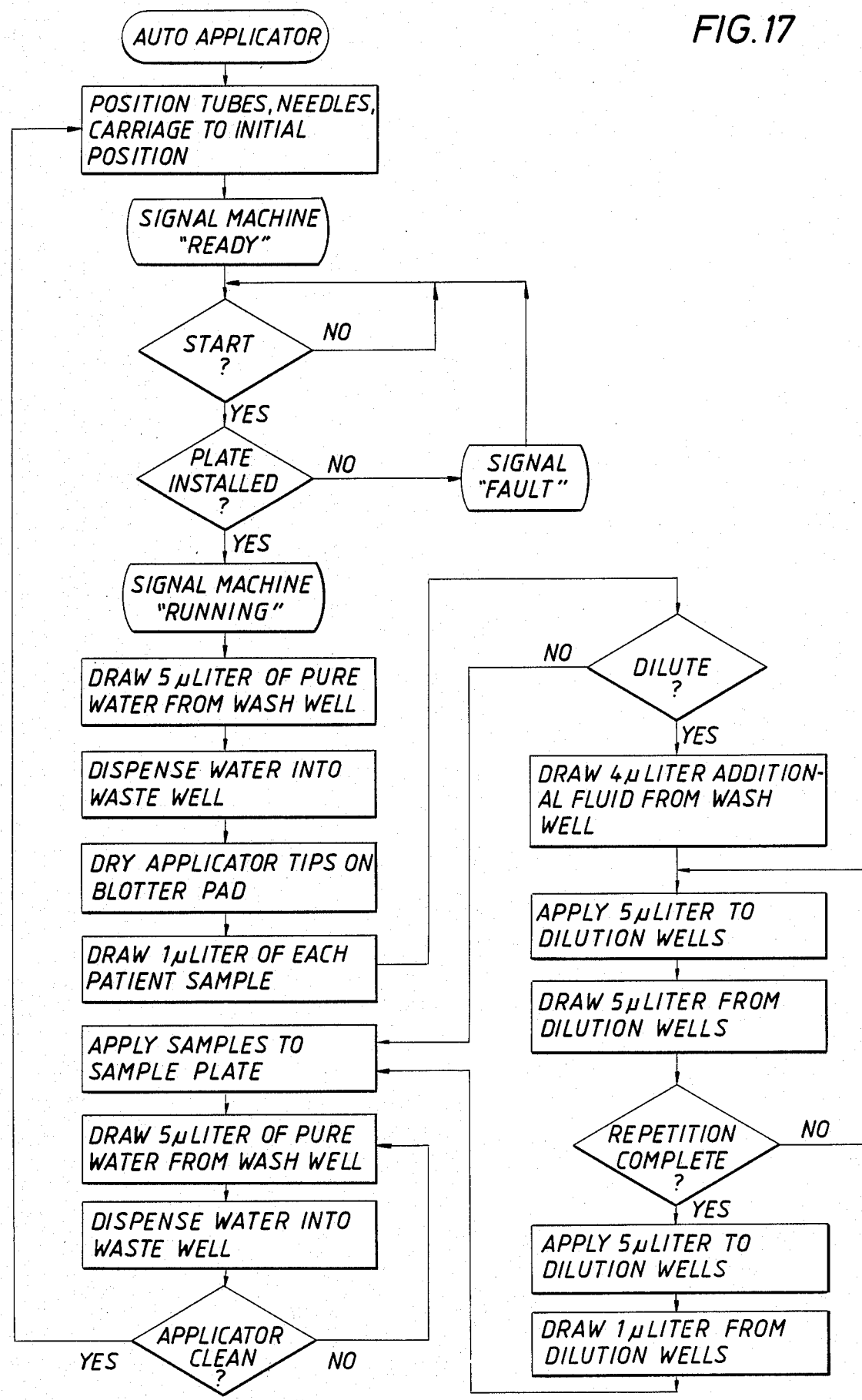
FIG. 17 is a functional flow chart illustrating the stored program in the microcomputer device for automatically washing, blotting, sampling and applying samples to the support medium strip.

FIG. 17 illustrates in flow chart form the operations of the CPU 201A under program control. The CPU 201A determines the validity of a command to start the processing by means of reading and decoding the binary coded data present at the input interface 201F which receives a signal from the interlock circuit 213. This operation insures that the plate 16 is fully inserted into the carriage.

The CPU 201A causes the motors 40, 116 or 126 to turn in the required direction by means of writing the appropriate binary coded data to the output interface circuit 201E which is connected to the motor drive circuits 202, 203 and 204. The microprocessor CPU 201A then causes the mechanism movement to stop precisely when the required location is reaches by writing the appropriate binary coded data to the output interface circuit 201E which is connected to the motor drive circuits 202, 203, 204 to disable the drive and then writing the appropriate binary coded data to the output interface 201E which is connected to the motor break circuits 205, 206, 207 to apply electronic breaking.

The microprocessor circuit 201A then signals that the pipetting apparatus is ready or that a plate has been complete or that a failure has occurred by means of writing the appropriate binary coded data to the output interface circuit 201E connected to the alarm circuit 211 to sound an alarm.

The timer 201D of FIG. 16 is used by the microprocessor CPU 201A to determine electrical or mechanical failures of the positioning mechanism. This is accomplished by means of measuring the elapsed time during a command to drive any motor. If the event is not completed within the prescribed length of time, the drive command is aborted and the alarm is activated by means of the microprocessor CPU 201A writing the appropriate binary coded data to the output interface connected to the alarm circuit 211. The timer 201D is also used to determine the repetition rate of the alarm thereby allowing the microprocessor circuit CPU 201A to encript and communicate to the operator the nature of the failure.

As shown in FIG. 17, once the automatic pipetting apparatus of the invention is running, a wide variety of different applications may be achieved. The sequence of operations shown in FIG. 17 is preferred in that first, five microliters of cleansing agent such as distilled water is aspirated into the barrels of the pipettes from the wash well. Next, the water in the barrels is dispensed into the waste well. Then the applicator tips are dried by lowering them to a blotter pad as illustrated in FIG. 5.

Next, the barrels are moved to their upward position with the plungers in their downward position, the carriage is moved rearward and the barrels are lowered into the sample chambers 24. The plungers are raised thereby drawing a small amount of each sample of liquid, for example, patient blood to be tested. Where no dilution of the blood samples is desired, the samples are applied precisely to the cellulose acetate or agarose strip. The barrels are raised again. Again, the carriage is moved forward until the wash well is beneath the barrels and the mounting plate is lowered such that distilled water is again drawn into the barrels and then dispensed into the waste well.

Where dilution of the sample liquids is desired, the sample plate of FIG. 2B may be substituted for that of FIG. 2 and the computer program illustrated by the flow chart of FIG. 17 branches to the dilute routine. A preferred routine for diluting the samples is to draw an additional four micro liters of fluid from the wash well. This action results in each of the barrels being filled with four micro liters of diluting fluid (e.g, water) and one micro liter of blood (or other liquid) sample. Next the entire five micro liters of fluid of each barrel is applied to the respective dilution chambers of the dilution row of the plate of FIG. 2B. This process may be repeated a desired number of times to effect moving of the sample with the dilution fluid (water). Finally a one micro liter sample of the diluted blood sample is drawn into each barrel according to the description presented previously. The routine then proceeds as described above where the one micro liter of diluted liquid sample is applied to the support medium.

The dilution routine described above is preferred, but other routines may be used to effect good mixing of the blood sample with diluting liquid. For example, a first predetermined amount of liquid sample in each barrel may be applied to the dilution wells. A predetermined amount of wash liquid may then be applied to the dilution wells. After mixing the combination of the wash liquid and liquid sample of the dilution wells, (for example by the mixing technique described above), a small amount of liquid samples is aspirated from the dilution wells and applied to the support medium.

The appendix to this specification includes a source listing of the computer program written in HD68P01V07 Hitachi Assembly language which is stored in the read only memory 201B so as to automatically control the pipetting, cleansing, blotting, diluting (at the operator's option) and other functions described above.

Various modifications and alterations in the described structures will be apparent to those skilled in the art of the foregoing description which does not depart from the spirit of the invention. For this reason, these changes are desired to be included in the appended claims. The appended claims recite the only limitation to the present invention and the descriptive manner which is employed for setting forth the embodiments and is to be interpreted as illustrative and not limitative.

APPENDIX TO SPECIFICATION

```
                          *** INTERNAL REGISTER MAP ***

**********************
                          * INPUT/OUTPUT PORTS *
                          **********************

9   0000                P1DDR     EQU    $0000       * Port 1 Data Dir. Reg.

10   0001                P2DDR     EQU    $0001       * Port 2 Data Dir. Reg.

12   0002                PORT1     EQU    $0002       * Port 1 Data Register

* Bit0= (P10)  Carriage Tbrake
                          * Bit1= (P11)  Not used
                          * Bit2= (P12)  Tube Tbrake
                          * Bit3= (P13)  Not used
                          * Bit4= (P14)  Needle Tbrake
                          * Bit5= (P15)  Needle Motor enable
                          * Bit6= (P16)  Tube Motor enable
                          * Bit7= (P17)  Carriage Motor enable 24   0003                PORT2     EQU    $0003       * Port 2 Data Register

* Bit0= (P20)  Not used
                          * Bit1= (P21)  Beeper output
                          * Bit2= (P22)  Not used
                          * Bit3= (P23)  Not used
                          * Bit4= (P24)  Not used 32   0004                P3DDR     EQU    $0004       * Port 3 Data Dir. Reg 33   0005                P4DDR     EQU    $0005       * Port 4 Data Dir. Reg 35   0006                PORT3     EQU    $0006       * Port 3 Data Register

* BIT0= (P30)   DIRECTION BIT FOR CRG MOTOR
                          * BIT1= (P31)   DIRECTION BIT FOR CRG MOTOR
                          * BIT2= (P32)   DIRECTION BIT FOR TUBES MOTOR
                          * BIT3= (P33)   DIRECTION BIT FOR TUBES MOTOR
                          * BIT4= (P34)   DIRECTION BIT FOR NEEDLES MOTOR
                          * BIT5= (P35)   DIRECTION BIT FOR NEEDLES MOTOR
                          * BIT6= (P36)   NOT USED
                          * Bit7= (P37)   NOT USED
                          * SC1= Not used
                          * SC2= Not used 48   0007                PORT4     EQU    $0007       * Port 4 Data Register

* Bit0= (P40)  Home position for carrier
                          * Bit1= (P41)  Home position for tubes
                          * Bit2= (P42)  Home position for needles
                          * Bit3= (P43)  Carrier position
                          * Bit4= (P44)  Tubes position
                          * Bit5= (P45)  Needle position
                          * Bit6= (P46)  Not used
                          * Bit7= (P47)  Not used
```

```
59                              ********************
60                              * TIMER REGISTERS *
61                              ********************
62
63      0008            TCSREG    EQU     $0008       * Timer Control Stat
                                                        us Reg.
64
65                      * BIT0= (OLVL) POL of Port2-1 When Output Com
                                                        pare
66                      * BIT1= (IEDG) Polarity of Capture Clock
67                      * BIT2= (ETOI) Enable Overflow IRQ2
68                      * BIT3= (EOCI) Enable Output Compare IRQ2
69                      * BIT4= (EICI) Enable Input Capture IRQ
70                      * BIT5= (TOF)  Timer Overflow Flag
71                      * BIT6= (OCF)  Output Compare Flag
72                      * BIT7= (ICF)  Input  Capture Flag
73
74      0009            FRCMSB    EQU     $0009       * Free Running Count
                                                        er MSB.
75      000A            FRCLSB    EQU     $000A       * Free Running Count
                                                        er LSB
76
77      000B            OCRMSB    EQU     $000B       * Output Capture Reg
                                                        MSB
78      000C            OCRLSB    EQU     $000C       * Output Compare Reg
                                                        LSB
79
80      000D            ICRMSB    EQU     $000D       * Input Capture Reg
                                                        MSB
81      000E            ICRLSB    EQU     $000E       * Input Capture Reg
                                                        LSB
82
83                              ******************************
84                              * PORT IRQ CONTROL REGISTER *
85                              ******************************
86
87      000F            P3SREG    EQU     $000F       * Port 3 Status Reg.
88
89                      * Bit0=
90                      * Bit1=
91                      * Bit2=
92                      * Bit3= PORT3 Latch Enable
93                      * Bit4= OSS (Output Strobe Sel.)
94                      * Bit5=
95                      * Bit6= IS3 IRQ1 Enable
96                      * Bit7= IS3 Flag Bit
97
98                              **************************
99                              * SERIAL PORT REGISTERS *
100                             **************************
101
102     0010            RMCREG    EQU     $0010       * Rate Mode Control
                                                        Reg
103
104                     * Bit0= (SS0) Baud Rate Select
105                     * Bit1= (SS1) Baud Rate Select
106                     * Bit2= (CC0) Format Clk Source
107                     * Bit3= (CC1) Format Clk Source
108                     * Bit4=
109                     * Bit5=
110                     * Bit6=
111                     * Bit7=
112
113     0011            TRCSRG    EQU     $0011       * Xmit Recieve Contr
                                                        ol & Status
114
115                     * Bit0= (WU)  Wake-up
116                     * Bit1= (TE)  Xmit Enable
117                     * Bit2= (TIE) Xmit IRQ2 Enable
118                     * Bit3= (RE)  Recv Enable
119                     * Bit4= (RIE) Recv IRQ2 Ebable
120                     * Bit5= (TDRE) Xmit Data Reg Empty Flag
```

```
121                                     * Bit6= (ORDE) Overrun Framing Error
122                                     * Bit7= (RDRF) Recieve Data Reg Full
123
124     0012                    RCVREG    EQU     $0012    * Receive Data Regis
                                                            ter
125     0013                    XMTREG    EQU     $0013    * Transmit Data Regi
                                                            ster
126
127                             ************************************
128                             * RAM AND EPROM CONTROL REGISTERS *
129                             ************************************
130
131     0014                    RAMROM    EQU     $0014    * Ram Eprom Control
                                                            Reg.
132
133                             * Bit0= (PLC) Programing Latch Control
134                             * Bit1= (PPC) Programing Power Control
135                             * Bit2=
136                             * Bit3=
137                             * Bit4=
138                             * Bit5=
139                             * Bit6= (RAME) Enable Ram Addressing
140                             * Bit7= (STBY PWR) Standby Power Status Flag
141                             **** $0015-$001F RESERVED ! ****
142
143
144                             *****************************
145                             * STANDBY RAM ($0080-$00BF) *
146                             *****************************
147
148
149                             *****************************
150                             * TEMPORARY RAM ($00A0-$00FF) *
151                             *****************************
152
153     0080                    IRQMSK    EQU     $80      * DEBOUNCE MASK STAR
                                                            T SWITCH
154
155     0040                    TUBEENB   EQU     $40      *TUBE DRIVE ENABLE
156     0008                    TUBEMOTP  EQU     $08      *TUBE MOTOR DRIVE PO
                                                            SITIVE.
157     0002                    TUBESW1   EQU     $02      *TUBE HOME SWITCH.
158     0004                    TUBETBRK  EQU     $04      *TUBE TRIAC BRAKE
159     0004                    TUBEMOTN  EQU     $04      *TUBE MOTOR DRIVE NE
                                                            GATIVE.
160     0010                    TUBESW2   EQU     $10      *TUBE DOWN POSITION
                                                            SWITCH.
161     00F3                    TUBEMSK   EQU     $F3      *MASKS OFF THE TUBE
                                                            DIRECTION BITS TO A
                                                            0.
162
163     0080                    CRGENB    EQU     $80      *CARRIAGE DRIVE ENAB
                                                            LE
164     0002                    CRGMOTP   EQU     $02      *CARRIAGE MOTOR DRIV
                                                            E POSTIVE.
165     0001                    CRGSW1    EQU     $01      *CARRIAGE HOME POSIT
                                                            ION SWITCH.
166     0001                    CRGTBRK   EQU     $01      *CARRIAGE TRIAC BRAK
                                                            E
167     0001                    CRGMOTN   EQU     $01      *CARRIAGE MOTOR DRIV
                                                            E NEGATIVE.
168     0008                    CRGSW2    EQU     $08      *CARRIAGE LOCATION S
                                                            WITCH.
169     00FC                    CRGMSK    EQU     $FC      *MASKS OFF THE CRG D
                                                            IRECTION BIT TO A 0.
170
171     0020                    NDLENB    EQU     $20      *MASK OFF THE NEEDLE
                                                            DIRECTION BITS TO A
                                                            0
172     0020                    NDLMOTP   EQU     $20      *NEEDLE MOTOR DRIVE
                                                            POSTIVE.
173     0004                    NDLSW1    EQU     $04      *NEEDLE HOME POSITIO
```

| | | | | | |
|---|---|---|---|---|---|
| 174 | 0010 | NDLTBRK | EQU | $10 | *NEEDLE TRIAC BRAKE N SWITCH. |
| 175 | 0010 | NDLMOTN | EQU | $10 | *NEEDLE MOTOR DRIVE NEGATIVE. |
| 176 | 0020 | NDLSW2 | EQU | $20 | *NEEDLE LOCATION SWITCH. |
| 177 | 00CF | NDLMSK | EQU | $CF | *MASK OFF THE NDL DIRECTION BIT TO A 0. |
| 178 | | | | | |
| 179 | 0003 | CLEANYET | EQU | $03 | *HOW MANY TIMES TO CYCLE THROUGH THE WASH CYCLE. |
| 180 | 0040 | TRAY | EQU | $40 | *TO MAKE SURE THE TRAY IS ALL THE IN. |
| 181 | 0001 | WASH | EQU | $01 | *CARRIAGE LOCATION ONE. |
| 182 | 0002 | WASTE | EQU | $02 | *CARRIAGE LOCATION TWO. |
| 183 | 0003 | BLOT | EQU | $03 | *CARRIAGE LOCATION THREE. |
| 184 | 0004 | SAMPWELL | EQU | $04 | *CARRIAGE LOCATION FOUR. |
| 185 | 0005 | DULUTER | EQU | $05 | |
| 186 | 0006 | PLATE | EQU | $06 | *CARRIAGE LOCATION FIVE. |
| 187 | 0001 | NDL1UL | EQU | $01 | *NEEDLE LOCATION ONE. |
| 188 | 0002 | NDL5UL | EQU | $02 | *NEEDLE LOCATION TWO. |
| 189 | 0001 | ERROR1 | EQU | $01 | *TUBES NOT AT HOME POSITION. |
| 190 | 0002 | ERROR2 | EQU | $02 | *MOTOR NOT DRIVING. |
| 191 | 0003 | ERROR3 | EQU | $03 | *TRAY IS NOT ALL THE WAY IN. |
| 192 | 0004 | ERROR4 | EQU | $04 | |
| 193 | 0004 | ETOI | EQU | $04 | *TIMER OVERFLOW FLAG IN THE TCSREG. |
| 194 | 00FF | STACK | EQU | $FF | *TOP OF RAM. |
| 195 | 0015 | ALLBRAKE | EQU | $15 | |
| 196 | 00E0 | ALLENB | EQU | $E0 | *ALL MOTOR ENABLE |
| 197 | 0002 | BRAKEPRT | EQU | PORT1 | |
| 198 | 000F | SWBOUNCE | EQU | $0F | *WAITING FOR TUBE SWITCH TO STOP BOUNCING. |
| 199 | 5000 | JOGTIME | EQU | $5000 | |
| 200 | 02FF | TONE1 | EQU | $02FF | *TUBE HOME POS. ERROR TONE. |
| 201 | 04FF | TONE2 | EQU | $04FF | *MOTOR NOT REACHING LIMIT SWITCH TONE |
| 202 | 08FF | TONE3 | EQU | $08FF | *TRAY NOT IN TONE. |
| 203 | 0FFF | TONE4 | EQU | $0FFF | *SWITCH NOT CLOSED ERROR. |
| 204 | 1FFF | TONE5 | EQU | $1FFF | *UNKNOWN ERROR. |
| 205 | 1FFF | TONE | EQU | $1FFF | *READY FOR OPERATION TONE. |
| 206 | 0007 | SWPRT | EQU | PORT4 | *SWITCH PORT, PORT4 |
| 207 | 0006 | MOTORPRT | EQU | PORT3 | *MOTOR PORT, PORT3 |
| 208 | 00FF | OFFSW | EQU | $00FF | |
| 209 | 00AF | SOAKTIME | EQU | $00AF | *PAUSE TIME. |
| 210 | 0010 | BLOTIME | EQU | $0010 | |
| 211 | 0080 | | ORG | $0080 | |
| 212 | 0080 | WASHTIMS | RMB | 1 | |
| 213 | 0081 | TONES | RMB | 2 | |
| 214 | 0083 | WATCHDOG | RMB | 1 | |
| 215 | 0084 | ENABLE | RMB | 1 | * MOTOR CONTROL BLOCK ENABLE |
| 216 | 0085 | DIRECT | RMB | 1 | * MOTOR CONTROL BLOCK DIRECTION |
| 217 | 0086 | SWITCH | RMB | 1 | * MOTOR CONTROL BLOCK SWITCH |
| 218 | 0087 | TBRAKE | RMB | 1 | * MOTOR CONTROL BLOC |

```
219        0088                   MASK     RMB   1      K TRIAC BRAKE
                                                        * MOTOR CONTROL DIRE
                                                        CTION BIT MASK
220        0089                   CRGPOS   RMB   1
221        008A                   NDLPOS   RMB   1
222        008B                   STATUS   RMB   1      * Mode Flag
223        008C                   COUNT    RMB   1
224                                                     ****************************
225                                        MAC   START
226                               &L       LDAA  ENABLE
227                                        COMA
228                                        ANDA  BRAKEPRT
229                                        STAA  BRAKEPRT   * DISABLE DRIVE
230                                        LDAA  MASK
231                                        ANDA  MOTORPRT   * ZERO DIRECTION BIT
                                                            S
232                                        ORAA  DIRECT     * GET REQUIRED DIREC
                                                            TION
233                                        STAA  MOTORPRT
234                                        LDAA  ENABLE
235                                        ORAA  BRAKEPRT
236                                        STAA  BRAKEPRT   * ENABLE
237  245R 008D                             MEN
238                                        MAC   STOP
239                               &L       LDAA  ENABLE
240                                        COMA
241                                        ANDA  BRAKEPRT   * DISABLE DRIVE
242                                        ORAA  TBRAKE     * TRIAC BRAKE
243                                        STAA  BRAKEPRT   * BRAKE AND DISABLE
244                                        LDAA  MASK
245                                        ANDA  MOTORPRT
246                                        STAA  MOTORPRT   * DRIVE FAST STOP
247                                        LDAA  ENABLE
248                                        ORAA  BRAKEPRT
249                                        STAA  BRAKEPRT   * DRIVE FAST STOP
250  490  008D                             MEN
251                                                     ****************************
252        F800                            ORG   #F800
253   2R   F800  0F                INIT    SEI
254    8   F801  7F 008B                   CLR   STATUS
255   14   F804  7F 008C                   CLR   COUNT
256   16   F807  86 02                     LDAA  #$02
257   20   F809  97 01                     STAA  P2DDR     *MAKES P21 AN OUTPUT
258   22   F80B  4F                        CLRA
259   26   F80C  97 08                     STAA  TCSREG
260   28   F80E  43                        COMA
261   30   F80F  C6 E0                     LDAB  #ALLENB
262   32   F811  53                        COMB
263   36   F812  97 00                     STAA  P1DDR     * PORT 1 ALL OUTPUT
264   40   F814  D7 02                     STAB  BRAKEPRT  * SET ALL TRIAC BRAK
                                                            E,DISABLE DRIVE
265   44   F816  97 04                     STAA  P3DDR     * PORT 3 ALL OUTPUT
266   47   F818  CE 7FFF                   LDX   #$7FFF
267   6R   F81B  7F 0006          !1       CLR   MOTORPRT  * MOTOR DRIVES FAST
                                                            STOP
268    8   F81E  C6 E0                     LDAB  #ALLENB
269   11   F820  DA 02                     ORAB  BRAKEPRT
270   15   F822  D7 02                     STAB  BRAKEPRT  * ENABLE DRIVE FOR F
                                                            AST STOP
271   18   F824  8E 00FF                   LDS   #STACK
272   22   F827  09                        DEX
273   26   F828  26 F1   (F81B)            BNE   !1
274   2R   F82A  0E                        CLI
275   11  *F82B  BD F9C9                   JSR   TUBEHOME
276   20  *F82E  BD F9E3                   JSR   CRGHOME
277   29  *F831  BD FA12                   JSR   NDLHOME
278   38  *F834  BD FB15                   JSR   BEEPER
279   44   F837  7F 0080                   CLR   WASHTIMS
280   46   F83A  86 80                     LDAA  #$80
281   51   F83C  B7 008B                   STAA  STATUS    * Mode READY
282   60   F83F  3E                        WAI
```

```
283   2R F840 C6 E0              EXEC   LDAB  #ALLENB
284    4 F842 53                        COMB
285    8 F843 D7 02                     STAB  BRAKEPRT  *SETS THE TRIAC BRAK
                                                        ES, AND DISENABLES T
                                                        HE MOTORS.
286   14 F845 7F 0006                   CLR   MOTORPRT  *MOTOR DRIVERS FAST
                                                        STOP.
287   16 F848 C6 E0                     LDAB  #ALLENB
288   19 F84A DA 02                     ORAB  BRAKEPRT
289   23 F84C D7 02                     STAB  BRAKEPRT  *ENABLES MOTOR DRIVE
                                                        RS FOR FAST STOP.
290   3R F84E CE 00FF        !7         LDX   #OFFSW
291   3R F851 96 07          !4         LDAA  SWPRT
292    5 F853 84 80                     ANDA  #IRQMSK
293    9 F855 27 F7  (F84E)             BEQ   !7
294   4R F857 09                        DEX
295    8 F858 26 F7  (F851)             BNE   !4
296
297   6R F85A 7D 008B                   TST   STATUS
298   10 F85D 26 01  (F860)             BNE   !2        * If Not = 0 Not INI
                                                        TL Mode
299   20 F85F 3B                        RTI
300   24 F860 2B 03  (F865)  !2         BMI   !3        * If -. READY Mode so
                                                        . go RUN
301   3R F862 7E F800                   JMP   INIT      * If + RUN Mode so g
                                                        o INIT
302   2R F865 86 7F          !3         LDAA  #$7F
303    7 F867 B7 008B                   STAA  STATUS    * Flag RUN mode
304    9 F86A 0E                        CLI
305   12 F86B 8E 00FF                   LDS   #STACK
306   14 F86E C6 01                     LDAB  #WASH
307   23 *F870 BD FAB7                  JSR   CRGLOC
308   32 *F873 BD F9D6                  JSR   TUBEDOWN
309   34 F876 C6 02                     LDAB  #NDL5UL
310   43 *F878 BD FAE6                  JSR   NDLLOC
311   52 *F87B BD F9C9                  JSR   TUBEHOME
312   54 F87E C6 02                     LDAB  #WASTE
313   63 *F880 BD FAB7                  JSR   CRGLOC
314   72 *F883 BD FA12                  JSR   NDLHOME
315   81 *F886 BD F9D6                  JSR   TUBEDOWN
316   90 *F889 BD F9C9                  JSR   TUBEHOME
317   92 F88C C6 03                     LDAB  #BLOT
318  101 *F88E BD FAB7                  JSR   CRGLOC
319  110 *F891 BD F9D6                  JSR   TUBEDOWN
320  119 *F894 BD FC33                  JSR   BLOTTER   *THE TIME THE TUBES
                                                        WILL STAY DOWN.
321  128 *F897 BD F9C9                  JSR   TUBEHOME
322  130 F89A C6 04                     LDAB  #SAMPWELL
323  139 *F89C BD FAB7                  JSR   CRGLOC
324  148 *F89F BD F9D6                  JSR   TUBEDOWN
325  150 F8A2 C6 01                     LDAB  #NDL1UL
326  159 *F8A4 BD FAE6                  JSR   NDLLOC
327  168 *F8A7 BD F9C9                  JSR   TUBEHOME
328  170 F8AA C6 03                     LDAB  #BLOT
329  179 *F8AC BD FAB7                  JSR   CRGLOC
330  188 *F8AF BD FA12                  JSR   NDLHOME
331  197 *F8B2 BD F9D6                  JSR   TUBEDOWN
332  206 *F8B5 BD FC33                  JSR   BLOTTER
333  215 *F8B8 BD F9C9                  JSR   TUBEHOME
334  217 F8BB C6 04                     LDAB  #SAMPWELL
335  226 *F8BD BD FAB7                  JSR   CRGLOC
336  235 *F8C0 BD F9D6                  JSR   TUBEDOWN
337  237 F8C3 C6 01                     LDAB  #NDL1UL
338  246 *F8C5 BD FAE6                  JSR   NDLLOC
339  255 *F8C8 BD F9C9                  JSR   TUBEHOME
340  258 F8CB 96 06                     LDAA  MOTORPRT
341  260 F8CD 84 50                     ANDA  #80
342  264 F8CF 26 3B  (F90C)             BNE   !10
343   2R F8D1 C6 01                     LDAB  #WASH
344   11 *F8D3 BD FAB7                  JSR   CRGLOC
345   20 *F8D6 BD F9D6                  JSR   TUBEDOWN
346   22 F8D9 C6 02                     LDAB  #NDL5UL
347   31 *F8DB BD FAE6                  JSR   NDLLOC
```

```
348   40 *F8DE  BD F9C9              JSR   TUBEHOME
349   42  F8E1  C6 05                LDAB  #DULUTER
350   51 *F8E3  BD FAB7              JSR   CRGLOC
351   60 *F8E6  BD FA12              JSR   NDLHOME
352   69 *F8E9  BD F9D6              JSR   TUBEDOWN
353   71  F8EC  C6 02                LDAB  #NDL5UL
354   80 *F8EE  BD FAE6              JSR   NDLLOC
355   89 *F8F1  BD FA12              JSR   NDLHOME
356   91  F8F4  C6 02                LDAB  #NDL5UL
357  100 *F8F6  BD FAE6              JSR   NDLLOC
358  109 *F8F9  BD FA12              JSR   NDLHOME
359  111  F8FC  C6 02                LDAB  #NDL5UL
360  120 *F8FE  BD FAE6              JSR   NDLLOC
361  129 *F901  BD FA12              JSR   NDLHOME
362  131  F904  C6 01                LDAB  #NDL1UL
363  140 *F906  BD FAE6              JSR   NDLLOC
364  149 *F909  BD F9C9              JSR   TUBEHOME
365   2R  F90C  C6 06          !10   LDAB  #PLATE
366   11 *F90E  BD FAB7              JSR   CRGLOC
367   20 *F911  BD FA12              JSR   NDLHOME
368   29 *F914  BD F9D6              JSR   TUBEDOWN
369   38 *F917  BD FAA8              JSR   SOAK
370   47 *F91A  BD F9C9              JSR   TUBEHOME
371   49  F91D  C6 03                LDAB  #BLOT
372   58 *F91F  BD FAB7              JSR   CRGLOC
373   67 *F922  BD F9D6              JSR   TUBEDOWN
374   76 *F925  BD FC33              JSR   BLOTTER
375   85 *F928  BD F9C9              JSR   TUBEHOME
376   2R  F92B  C6 01          !1    LDAB  #WASH
377   11 *F92D  BD FAB7              JSR   CRGLOC
378   20 *F930  BD F9D6              JSR   TUBEDOWN
379   22  F933  C6 02                LDAB  #NDL5UL
380   31 *F935  BD FAE6              JSR   NDLLOC
381   40 *F938  BD F9C9              JSR   TUBEHOME
382   42  F93B  C6 02                LDAB  #WASTE
383   51 *F93D  BD FAB7              JSR   CRGLOC
384   60 *F940  BD FA12              JSR   NDLHOME
385   69 *F943  BD F9D6              JSR   TUBEDOWN
386   78 *F946  BD F9C9              JSR   TUBEHOME
387   22  F949  B6 0080              LDAA  WASHTIMS
388   84  F94C  81 00                CMPA  #$00
389   88  F94E  27 08   (F958)       BEQ   !5
390   2R  F950  81 01                CMPA  #$01
391    6  F952  27 2F   (F983)       BEQ   !6
392   2R  F954  81 02                CMPA  #$02
393    6  F956  27 12   (F96A)       BEQ   !8
394   2R  F958  C6 03          !5    LDAB  #BLOT
395   11 *F95A  BD FAB7              JSR   CRGLOC
396   14  F95D  CE 5000              LDX   #JOGTIME  *HOW LONG TO LEAVE T
                                                    HE MOTORS ON.
397   16  F960  86 02                LDAA  #CRGMOTP
398   21  F962  B7 0085              STAA  DIRECT
399   30 *F965  BD F990              JSR   JOG
400   34  F968  20 10   (F97A)       BRA   !9
401   2R  F96A  C6 03          !8    LDAB  #BLOT
402   11 *F96C  BD FAB7              JSR   CRGLOC
403   13  F96F  86 01                LDAA  #CRGMOTN
404   18  F971  B7 0085              STAA  DIRECT
405   21  F974  CE 5000              LDX   #JOGTIME  *HOW LONG TO LEAVE T
                                                    HE MOTORS ON
406   30 *F977  BD F990              JSR   JOG
407   9R*F97A  BD F9D6          !9    JSR   TUBEDOWN
408   18 *F97D  BD FC33              JSR   BLOTTER
409   27 *F980  BD F9C9              JSR   TUBEHOME
410   6R  F983  7C 0080         !6    INC   WASHTIMS
411    8  F986  86 03                LDAA  #CLEANYET
412   12  F988  B1 0080              CMPA  WASHTIMS
413   16  F98B  26 9E   (F92B)       BNE   !1
414   3R  F98D  7E F800              JMP   INIT
415   9R*F990  BD FC42       JOG     JSR   BRAKOFF
416       F993                       START
```

```
416  13  F993  B6 0084       +              LDAA    ENABLE
416  15  F996  43            +              COMA
416  18  F997  94 02         +              ANDA    BRAKEPRT
416  22  F999  97 02         +              STAA    BRAKEPRT    * DISABLE DRIVE
416  26  F99B  B6 0088       +              LDAA    MASK
416  29  F99E  94 06         +              ANDA    MOTORPRT    * ZERO DIRECTION BIT
                                                                 S
416  33  F9A0  BA 0085       +              ORAA    DIRECT      * GET REQUIRED DIREC
                                                                 TION
416  37  F9A3  97 06         +              STAA    MOTORPRT
416  41  F9A5  B6 0084       +              LDAA    ENABLE
416  44  F9A8  9A 02         +              ORAA    BRAKEPRT
416  48  F9AA  97 02         +              STAA    BRAKEPRT    * ENABLE
417  4R  F9AC  09                  !1       DEX
418   8  F9AD  26 FD  (F9AC)          BNE    !1
419      F9AF                                  STOP
419  4R  F9AF  B6 0084       +              LDAA    ENABLE
419   6  F9B2  43            +              COMA
419   9  F9B3  94 02         +              ANDA    BRAKEPRT    * DISABLE DRIVE
419  13  F9B5  BA 0087       +              ORAA    TBRAKE      * TRIAC BRAKE
419  17  F9B8  97 02         +              STAA    BRAKEPRT    * BRAKE AND DISABLE
419  21  F9BA  B6 0088       +              LDAA    MASK
419  24  F9BD  94 06         +              ANDA    MOTORPRT
419  28  F9BF  97 06         +              STAA    MOTORPRT    * DRIVE FAST STOP
419  32  F9C1  B6 0084       +              LDAA    ENABLE
419  35  F9C4  9A 02         +              ORAA    BRAKEPRT
419  39  F9C6  97 02         +              STAA    BRAKEPRT    * DRIVE FAST STOP
420  44  F9C8  39                           RTS
421  2R  F9C9  C6 01              TUBEHOME  LDAB    #$01
422   5  F9CB  CE F9D1                      LDX     #!1
423   8  F9CE  7E FB69                      JMP     DRIVE!9
424     F9D1  40                    !1       FCB     TUBEENB
425     F9D2  08                             FCB     TUBEMOTP
426     F9D3  02                             FCB     TUBESW1
427     F9D4  04                             FCB     TUBETBRK
428     F9D5  F3                             FCB     TUBEMSK
429  2R  F9D6  C6 01              TUBEDOWN  LDAB    #$01
430   5  F9D8  CE F9DE                      LDX     #!1
431   8  F9DB  7E FB66                      JMP     DRIVE
432     F9DE  40                    !1       FCB     TUBEENB
433     F9DF  04                             FCB     TUBEMOTN
434     F9E0  10                             FCB     TUBESW2
435     F9E1  04                             FCB     TUBETBRK
436     F9E2  F3                             FCB     TUBEMSK
437  6R  F9E3  7F 0089            CRGHOME   CLR     CRGPOS
438  15 *F9E6  BD FA2D                      JSR     CHECKTUB
439  18  F9E9  CE F9F1                      LDX     #!1
440  20  F9EC  C6 01                        LDAB    #$01
441  23  F9EE  7E FB66                      JMP     DRIVE
442     F9F1  80                    !1       FCB     CRGENB
443     F9F2  02                             FCB     CRGMOTP
444     F9F3  01                             FCB     CRGSW1
445     F9F4  01                             FCB     CRGTBRK
446     F9F5  FC                             FCB     CRGMSK
447  9R*F9F6  BD FA2D             CRGBACK   JSR     CHECKTUB
448  12  F9F9  CE F9FF                      LDX     #!1
449  15  F9FC  7E FB66                      JMP     DRIVE
450     F9FF  80                    !1       FCB     CRGENB
451     FA00  01                             FCB     CRGMOTN
452     FA01  08                             FCB     CRGSW2
453     FA02  01                             FCB     CRGTBRK
454     FA03  FC                             FCB     CRGMSK
455  9R*FA04  BD FA2D             CRGFRONT  JSR     CHECKTUB
456  12  FA07  CE FA0D                      LDX     #!1
457  15  FA0A  7E FB66                      JMP     DRIVE
458     FA0D  80                    !1       FCB     CRGENB
459     FA0E  02                             FCB     CRGMOTP
460     FA0F  08                             FCB     CRGSW2
461     FA10  01                             FCB     CRGTBRK
462     FA11  FC                             FCB     CRGMSK
463  6R  FA12  7F 008A            NDLHOME   CLR     NDLPOS
```

```
464   8  FA15  C6 01                        LDAB    #$01
465  11  FA17  CE FA1D                      LDX     #!1
466  14  FA1A  7E FB69                      JMP     DRIVE!9
467      FA1D  20              !1           FCB     NDLENB
468      FA1E  20                           FCB     NDLMOTP
469      FA1F  04                           FCB     NDLSW1
470      FA20  10                           FCB     NDLTBRK
471      FA21  CF                           FCB     NDLMSK
472  3R  FA22  CE FA28         NDL1UL5      LDX     #!1
473   6  FA25  7E FB69                      JMP     DRIVE!9
474      FA28  20              !1           FCB     NDLENB
475      FA29  10                           FCB     NDLMOTN
476      FA2A  20                           FCB     NDLSW2
477      FA2B  10                           FCB     NDLTBRK
478      FA2C  CF                           FCB     NDLMSK
479  2R  FA2D  86 0F           CHECKTUB     LDAA    #SWBOUNCE
480  3R  FA2F  CE 03FF         !2           LDX     #$03FF
481  4R  FA32  09              !1           DEX
482   8  FA33  26 FD   (FA32)               BNE     !1
483  2R  FA35  4A                           DECA
484   6  FA36  26 F7   (FA2F)               BNE     !2
485  2R  FA38  86 02                        LDAA    #TUBESW1
486   5  FA3A  94 07                        ANDA    SWPRT
487   9  FA3C  27 05   (FA43)               BEQ     !3
488  2R  FA3E  86 01                        LDAA    #ERROR1
489   5  FA40  7E FB38                      JMP     BEEPERRO
490  10  FA43  39              !3           RTS
491  3R  FA44  96 08           UPDATIME     LDAA    TCSREG   *CLEARS IRQ
492   6  FA46  96 09                        LDAA    TCSREG+1
493  12  FA48  7C 0083                      INC     WATCHDOG
494  16  FA4B  27 01   (FA4E)               BEQ     !1
495  26  FA4D  3B                           RTI
496      FA4E                  !1           STOP
496  4R  FA4E  B6 0084         +!1          LDAA    ENABLE
496   6  FA51  43              +            COMA
496   9  FA52  94 02           +            ANDA    BRAKEPRT  * DISABLE DRIVE
496  13  FA54  BA 0087         +            ORAA    TBRAKE    * TRIAC BRAKE
496  17  FA57  97 02           +            STAA    BRAKEPRT  * BRAKE AND DISABLE
496  21  FA59  B6 0088         +            LDAA    MASK
496  24  FA5C  94 06           +            ANDA    MOTORPRT
496  28  FA5E  97 06           +            STAA    MOTORPRT  * DRIVE FAST STOP
496  32  FA60  B6 0084         +            LDAA    ENABLE
496  35  FA63  9A 02           +            ORAA    BRAKEPRT
496  39  FA65  97 02           +            STAA    BRAKEPRT  * DRIVE FAST STOP
497  42  FA67  96 08                        LDAA    TCSREG
498  44  FA69  84 FB                        ANDA    #$FB
499  48  FA6B  97 08                        STAA    TCSREG
500  50  FA6D  0E                           CLI
501  52  FA6E  86 02                        LDAA    #ERROR2
502  55  FA70  7E FB38                      JMP     BEEPERRO
503  2R  FA73  86 40           TRAYIN       LDAA    #TRAY
504   5  FA75  94 07                        ANDA    SWPRT
505   9  FA77  26 01   (FA7A)               BNE     !1
506  14  FA79  39                           RTS
507  9R*FA7A  BD FA12          !1           JSR     NDLHOME
508  18 *FA7D  BD F9C9                      JSR     TUBEHOME
509  27 *FA80  BD FC33                      JSR     BLOTTER
510  29  FA83  C6 02                        LDAB    #NDL5UL
511  38 *FA85  BD FAE6                      JSR     NDLLOC
512  47  FA88  3E                           WAI
513  6R  FA89  FF 0081         FLASH        STX     TONES
514  9R*FA8C  BD FB18          !2           JSR     BEEPER!1
515  3R  FA8F  CE 0000         !3           LDX     #$0000
516  4R  FA92  08              !1           INX
517   8  FA93  26 FD   (FA92)               BNE     !1
518  4R  FA95  B6 008C                      LDAA    COUNT
519   6  FA98  4C                           INCA
520  11  FA99  B7 008C                      STAA    COUNT
521  13  FA9C  81 01                        CMPA    #$01
522  17  FA9E  26 EF   (FA8F)               BNE     !3
523  6R  FAA0  7F 008C                      CLR     COUNT
524  11  FAA3  FE 0081                      LDX     TONES
```

```
525  15  FAA6  20 E4     (FA8C)              BRA   !2
526  3R  FAA8  CE 00AF           SOAK       LDX   #SOAKTIME
527  3R  FAAB  96 08             !1         LDAA  TCSREG
528  6   FAAD  D6 09                        LDAB  FRCMSB
529  8   FAAF  84 20                        ANDA  #$20
530  12  FAB1  27 F8     (FAAB)             BEQ   !1
531  4R  FAB3  09                           DEX
532  8   FAB4  26 F5     (FAAB)             BNE   !1
533  13  FAB6  39                           RTS
534  2R  FAB7  17               CRGLOC     TBA
535  6   FAB8  F0 0089                      SUBB  CRGPOS
536  10  FABB  24 15     (FAD2)             BCC   !1
537  2R  FABD  50                           NEGB
538  7   FABE  B7 0089                      STAA  CRGPOS
539  9   FAC1  86 01                        LDAA  #CRGSW1
540  12  FAC3  94 07                        ANDA  SWPRT
541  16  FAC5  27 08     (FACF)             BEQ   !2
542  2R  FAC7  86 08                        LDAA  #CRGSW2
543  5   FAC9  94 07                        ANDA  SWPRT
544  9   FACB  26 02     (FACF)             BNE   !2
545  2R  FACD  CB 01                        ADDB  #$01
546  3R  FACF  7E FA04           !2         JMP   CRGFRONT
547  5R  FAD2  B7 0089           !1         STAA  CRGPOS
548  7   FAD5  86 01                        LDAA  #CRGSW1
549  10  FAD7  94 07                        ANDA  SWPRT
550  14  FAD9  27 08     (FAE3)             BEQ   !3
551  2R  FADB  86 08                        LDAA  #CRGSW2
552  5   FADD  94 07                        ANDA  SWPRT
553  9   FADF  26 02     (FAE3)             BNE   !3
554  2R  FAE1  CB 01                        ADDB  #$01
555  3R  FAE3  7E F9F6           !3         JMP   CRGBACK
556  2R  FAE6  17               NDLLOC     TBA
557  6   FAE7  F0 008A                      SUBB  NDLPOS
558  10  FAEA  24 15     (FB01)             BCC   !1
559  2R  FAEC  50                           NEGB
560  7   FAED  B7 008A                      STAA  NDLPOS
561  9   FAF0  86 04                        LDAA  #NDLSW1
562  12  FAF2  94 07                        ANDA  SWPRT
563  16  FAF4  27 08     (FAFE)             BEQ   !2
564  2R  FAF6  86 20                        LDAA  #NDLSW2
565  5   FAF8  94 07                        ANDA  SWPRT
566  9   FAFA  26 02     (FAFE)             BNE   !2
567  2R  FAFC  CB 01                        ADDB  #$01
568  3R  FAFE  7E FA12           !2         JMP   NDLHOME
569  5R  FB01  B7 008A           !1         STAA  NDLPOS
570  7   FB04  86 04                        LDAA  #NDLSW1
571  10  FB06  94 07                        ANDA  SWPRT
572  14  FB08  27 08     (FB12)             BEQ   !3
573  2R  FB0A  86 20                        LDAA  #NDLSW2
574  5   FB0C  94 07                        ANDA  SWPRT
575  9   FB0E  26 02     (FB12)             BNE   !3
576  2R  FB10  CB 01                        ADDB  #$01
577  3R  FB12  7E FA22           !3         JMP   NDL1UL5
578  3R  FB15  CE 1FFF          BEEPER     LDX   #TONE
579  3R  FB18  D6 08             !1         LDAB  TCSREG
580  5   FB1A  C5 40                        BITB  #$40
581  9   FB1C  27 FA     (FB18)             BEQ   !1
582  2R  FB1E  C8 01                        EORB  #$01
583  6   FB20  D7 08                        STAB  TCSREG
584  9   FB22  D6 0C                        LDAB  OCRLSB
585  11  FB24  CB C8                        ADDB  #$C8
586  15  FB26  D7 0C                        STAB  OCRLSB
587  18  FB28  D6 0B                        LDAB  OCRMSB
588  20  FB2A  C9 00                        ADCB  #$00
589  24  FB2C  D7 0B                        STAB  OCRMSB
590  28  FB2E  09                           DEX
591  32  FB2F  26 E7     (FB18)             BNE   !1
592  3R  FB31  D6 08                        LDAB  TCSREG
593  5   FB33  84 FE                        ANDA  #$FE
594  9   FB35  D7 08                        STAB  TCSREG
595  14  FB37  39                           RTS
```

| | | | | | | | | |
|---|---|---|---|---|---|---|---|---|
| 596 | 2R | FB38 | 81 01 | | BEEPERRO | CMPA | #ERROR1 | |
| 597 | 6 | FB3A | 26 06 | (FB42) | | BNE | !1 | |
| 598 | 3R | FB3C | CE 02FF | | | LDX | #TONE1 | |
| 599 | 6 | FB3F | 7E FA89 | | | JMP | FLASH | |
| 600 | 2R | FB42 | 81 02 | | !1 | CMPA | #ERROR2 | |
| 601 | 6 | FB44 | 26 06 | (FB4C) | | BNE | !2 | |
| 602 | 3R | FB46 | CE 04FF | | | LDX | #TONE2 | |
| 603 | 6 | FB49 | 7E FA89 | | | JMP | FLASH | |
| 604 | 2R | FB4C | 81 03 | | !2 | CMPA | #ERROR3 | |
| 605 | 6 | FB4E | 26 06 | (FB56) | | BNE | !3 | |
| 606 | 3R | FB50 | CE 08FF | | | LDX | #TONE3 | |
| 607 | 6 | FB53 | 7E FA89 | | | JMP | FLASH | |
| 608 | 2R | FB56 | 81 04 | | !3 | CMPA | #ERROR4 | |
| 609 | 6 | FB58 | 26 06 | (FB60) | | BNE | !4 | |
| 610 | 3R | FB5A | CE 0FFF | | | LDX | #TONE4 | |
| 611 | 6 | FB5D | 7E FA89 | | | JMP | FLASH | |
| 612 | 3R | FB60 | CE 1FFF | | !4 | LDX | #TONE5 | |
| 613 | 6 | FB63 | 7E FA89 | | | JMP | FLASH | |
| 614 | 9R*FB66 | | BD FA73 | | DRIVE | JSR | TRAYIN | |
| 615 | 2R | FB69 | 0F | | !9 | SEI | | |
| 616 | 7 | FB6A | A6 00 | | | LDAA | 0,X | * SAVE MOTOR CONTROL BLOCK |
| 617 | 12 | FB6C | B7 0084 | | | STAA | ENABLE | |
| 618 | 17 | FB6F | A6 01 | | | LDAA | 1,X | |
| 619 | 22 | FB71 | B7 0085 | | | STAA | DIRECT | |
| 620 | 27 | FB74 | A6 02 | | | LDAA | 2,X | |
| 621 | 32 | FB76 | B7 0086 | | | STAA | SWITCH | |
| 622 | 37 | FB79 | A6 03 | | | LDAA | 3,X | |
| 623 | 42 | FB7B | B7 0087 | | | STAA | TBRAKE | |
| 624 | 47 | FB7E | A6 04 | | | LDAA | 4,X | |
| 625 | 52 | FB80 | B7 0088 | | | STAA | MASK | |
| 626 | 61 | *FB83 | BD FC42 | | | JSR | BRAKOFF | |
| 627 | 64 | FB86 | 96 08 | | | LDAA | TCSREG | |
| 628 | 67 | FB88 | 96 09 | | | LDAA | TCSREG+1 | |
| 629 | 69 | FB8A | 86 04 | | | LDAA | #ETOI | |
| 630 | 73 | FB8C | 97 08 | | | STAA | TCSREG | |
| 631 | 79 | FB8E | 7F 0083 | | | CLR | WATCHDOG | |
| 632 | 81 | FB91 | 0E | | | CLI | | |
| 633 | 85 | FB92 | B6 0086 | | | LDAA | SWITCH | *SWITCH MASK |
| 634 | 88 | FB95 | 94 07 | | | ANDA | SWPRT | |
| 635 | 92 | FB97 | 27 20 | (FBB9) | | BEQ | !1 | |
| 636 | | FB99 | | | | START | | |
| 636 | 4R | FB99 | B6 0084 | | + | LDAA | ENABLE | |
| 636 | 6 | FB9C | 43 | | + | COMA | | |
| 636 | 9 | FB9D | 94 02 | | + | ANDA | BRAKEPRT | |
| 636 | 13 | FB9F | 97 02 | | + | STAA | BRAKEPRT | * DISABLE DRIVE |
| 636 | 17 | FBA1 | B6 0088 | | + | LDAA | MASK | |
| 636 | 20 | FBA4 | 94 06 | | + | ANDA | MOTORPRT | * ZERO DIRECTION BITS |
| 636 | 24 | FBA6 | BA 0085 | | + | ORAA | DIRECT | * GET REQUIRED DIRECTION |
| 636 | 28 | FBA9 | 97 06 | | + | STAA | MOTORPRT | |
| 636 | 32 | FBAB | B6 0084 | | + | LDAA | ENABLE | |
| 636 | 35 | FBAE | 9A 02 | | + | ORAA | BRAKEPRT | |
| 636 | 39 | FBB0 | 97 02 | | + | STAA | BRAKEPRT | * ENABLE |
| 637 | 4R | FBB2 | B6 0086 | | !2 | LDAA | SWITCH | *AT SWITCH YET? |
| 638 | 7 | FBB5 | 94 07 | | | ANDA | SWPRT | |
| 639 | 11 | FBB7 | 26 F9 | (FBB2) | | BNE | !2 | |
| 640 | 2R | FBB9 | 5A | | !1 | DECB | | *ACCB IS KEEPING TRACK OF SWITCH CLOSURES. |
| 641 | 6 | FBBA | 26 02 | (FBBE) | | BNE | !3 | *IF THIS IS THE RIGHT SWITCH THEN STOP, IF NOT CONNTINUE. |
| 642 | 10 | FBBC | 20 30 | (FBEE) | | BRA | !4 | |
| 643 | | FBBE | | | !3 | START | | |
| 643 | 4R | FBBE | B6 0084 | | +!3 | LDAA | ENABLE | |
| 643 | 6 | FBC1 | 43 | | + | COMA | | |
| 643 | 9 | FBC2 | 94 02 | | + | ANDA | BRAKEPRT | |
| 643 | 13 | FBC4 | 97 02 | | + | STAA | BRAKEPRT | * DISABLE DRIVE |

| | | | | | | | | |
|---|---|---|---|---|---|---|---|---|
| 643 | 17 | FBC6 | B6 0088 | | + | | LDAA | MASK |
| 643 | 20 | FBC9 | 94 06 | | + | | ANDA | MOTORPRT * ZERO DIRECTION BITS |
| 643 | 24 | FBCB | BA 0085 | | + | | ORAA | DIRECT * GET REQUIRED DIRECTION |
| 643 | 28 | FBCE | 97 06 | | + | | STAA | MOTORPRT |
| 643 | 32 | FBD0 | B6 0084 | | + | | LDAA | ENABLE |
| 643 | 35 | FBD3 | 9A 02 | | + | | ORAA | BRAKEPRT |
| 643 | 39 | FBD5 | 97 02 | | + | | STAA | BRAKEPRT * ENABLE |
| 644 | 3R | FBD7 | CE 00FF | | !5 | | LDX | #OFFSW *MAKE SURE THAT IT IS REALLY OFF THE SWITCH. |
| 645 | 4R | FBDA | B6 0086 | | !6 | | LDAA | SWITCH |
| 646 | 7 | FBDD | 94 07 | | | | ANDA | SWPRT |
| 647 | 11 | FBDF | 27 F6 | (FBD7) | | | BEQ | !5 |
| 648 | 4R | FBE1 | 09 | | | | DEX | |
| 649 | 8 | FBE2 | 26 F6 | (FBDA) | | | BNE | !6 |
| 650 | 4R | FBE4 | B6 0086 | | !7 | | LDAA | SWITCH |
| 651 | 7 | FBE7 | 94 07 | | | | ANDA | SWPRT |
| 652 | 11 | FBE9 | 26 F9 | (FBE4) | | | BNE | !7 |
| 653 | 2R | FBEB | 5A | | | | DECB | |
| 654 | 6 | FBEC | 26 E9 | (FBD7) | | | BNE | !5 |
| 655 | | FBEE | | | !4 | | STOP | |
| 655 | 4R | FBEE | B6 0084 | | +!4 | | LDAA | ENABLE |
| 655 | 6 | FBF1 | 43 | | + | | COMA | |
| 655 | 9 | FBF2 | 94 02 | | + | | ANDA | BRAKEPRT * DISABLE DRIVE |
| 655 | 13 | FBF4 | BA 0087 | | + | | ORAA | TBRAKE * TRIAC BRAKE |
| 655 | 17 | FBF7 | 97 02 | | + | | STAA | BRAKEPRT * BRAKE AND DISABLE |
| 655 | 21 | FBF9 | B6 0088 | | + | | LDAA | MASK |
| 655 | 24 | FBFC | 94 06 | | + | | ANDA | MOTORPRT |
| 655 | 28 | FBFE | 97 06 | | + | | STAA | MOTORPRT * DRIVE FAST STOP |
| 655 | 32 | FC00 | B6 0084 | | + | | LDAA | ENABLE |
| 655 | 35 | FC03 | 9A 02 | | + | | ORAA | BRAKEPRT |
| 655 | 39 | FC05 | 97 02 | | + | | STAA | BRAKEPRT * DRIVE FAST STOP |
| 656 | 42 | FC07 | 96 08 | | | | LDAA | TCSREG |
| 657 | 44 | FC09 | 84 FB | | | | ANDA | #$FB |
| 658 | 48 | FC0B | 97 08 | | | | STAA | TCSREG |
| 659 | 54 | FC0D | 7F 0083 | | | | CLR | WATCHDOG |
| 660 | 3R | FC10 | 96 08 | | !10 | | LDAA | TCSREG *CHECKING THE TIMER OVERFLOW BIT. |
| 661 | 6 | FC12 | D6 09 | | | | LDAB | TCSREG+1 |
| 662 | 8 | FC14 | 84 20 | | | | ANDA | #$20 |
| 663 | 12 | FC16 | 27 F8 | (FC10) | | | BEQ | !10 |
| 664 | 6R | FC18 | 7C 0083 | | | | INC | WATCHDOG *HOW LONG TO WAIT BEFORE CHECKING SWITCH |
| 665 | 10 | FC1B | B6 0083 | | | | LDAA | WATCHDOG |
| 666 | 12 | FC1E | 81 03 | | | | CMPA | #$03 |
| 667 | 16 | FC20 | 26 EE | (FC10) | | | BNE | !10 |
| 668 | 6R | FC22 | 7F 0083 | | | | CLR | WATCHDOG |
| 669 | 10 | FC25 | B6 0086 | | | | LDAA | SWITCH |
| 670 | 13 | FC28 | 94 07 | | | | ANDA | SWPRT |
| 671 | 17 | FC2A | 27 05 | (FC31) | | | BEQ | !11 |
| 672 | 2R | FC2C | 86 04 | | | | LDAA | #ERROR4 |
| 673 | 5 | FC2E | 7E FB38 | | | | JMP | BEEPERRO |
| 674 | 10 | FC31 | 39 | | !11 | | RTS | |
| 675 | 15 | FC32 | 39 | | | | RTS | |
| 676 | 3R | FC33 | CE 0010 | | BLOTTER | | LDX | #BLOTIME |
| 677 | 3R | FC36 | 96 08 | | !1 | | LDAA | TCSREG |
| 678 | 6 | FC38 | D6 09 | | | | LDAB | FRCMSB |
| 679 | 8 | FC3A | 84 20 | | | | ANDA | #$20 |
| 680 | 12 | FC3C | 27 F8 | (FC36) | | | BEQ | !1 |
| 681 | 4R | FC3E | 09 | | | | DEX | |
| 682 | 8 | FC3F | 26 F5 | (FC36) | | | BNE | !1 |
| 683 | 13 | FC41 | 39 | | | | RTS | |
| 684 | 4R | FC42 | B6 0087 | | BRAKOFF | | LDAA | TBRAKE |
| 685 | 6 | FC45 | 43 | | | | COMA | |
| 686 | 9 | FC46 | 94 02 | | | | ANDA | BRAKEPRT |
| 687 | 13 | FC48 | 97 02 | | | | STAA | BRAKEPRT |
| 688 | 15 | FC4A | 4F | | | | CLRA | |
| 689 | 2R | FC4B | 4A | | !1 | | DECA | |
| 690 | 6 | FC4C | 26 FD | (FC4B) | | | BNE | !1 |

```
691   11   FC4E   39                    RTS
692        FFF0                         ORG    $FFF0
693        FFF0   F800                  FDB    INIT       * SCI OF THE TCSREG.

694        FFF2   FA44                  FDB    UPDATIME   * TIMER OVERFLOW BIT
695        FFF4   F800                  FDB    INIT       * OCI OF THE TCSREG.

696        FFF6   F800                  FDB    INIT       * ICI OF THE TCSREG.

697        FFF8   F840                  FDB    EXEC       * IRQ
698        FFFA   F800                  FDB    INIT       * SWI
699        FFFC   F800                  FDB    INIT       * NMI
700        FFFE   F800                  FDB    INIT       * RESET
701        0000                         END
```

NO ERRORS DETECTED

```
0015 ALLBRAKE   195
00E0 ALLENB     196   261  268  283  287
FB15 BEEPER     578   278  514
FB38 BEEPERRO   596   489  502  673
0003 BLOT       183   317  328  371  394  401
0010 BLOTIME    210   676
FC33 BLOTTER    676   320  332  374  408  509
0002 BRAKEPRT   197   264  269  270  285  288  289  416  416  416
                      416  419  419  419  419  496  496  496  496
                      636  636  636  636  643  643  643  643  655
                      655  655  655  686  687
     FC42 BRAKOFF    684   415  626
FA2D CHECKTUB   479   438  447  455
0003 CLEANYET   179   411
008C COUNT      223   255  518  520  523
F9F6 CRGBACK    447   555
0080 CRGENB     163   442  450  458
FA04 CRGFRONT   455   546
F9E3 CRGHOME    437   276
FAB7 CRGLOC           307  313  318  323  329  335  344  350  366
                534   372  377  383  395  402
0001 CRGMOTN    167   403  451
0002 CRGMOTP    164   397  443  459
00FC CRGMSK     169   446  454  462
0089 CRGPOS     220   437  535  538  547
0001 CRGSW1     165   444  539  548
0008 CRGSW2     168   452  460  542  551
0001 CRGTBRK    166   445  453  461
0085 DIRECT     216   398  404  416  619  636  643
FB66 DRIVE      614   423  431  441  449  457  466  473
0005 DULUTER    185   349
0084 ENABLE     215   416  419  419  496  496  617  636  636
                      643  643  655  655
0001 ERROR1     189   488  596
0002 ERROR2     190   501  600
0003 ERROR3     191   604
0004 ERROR4     192   608  672
0004 ETOI       193   629
F840 EXEC       283   697
FA89 FLASH      513   599  603  607  611  613
000A FRCLSB      75
0009 FRCMSB      74   528  678
000E ICRLSB      81
000D ICRMSB      80
F800 INIT       253   301  414  693  695  696  698  699  700
0080 IRQMSK     153   292
F990 JOG        415   399  406
5000 JOGTIME    199   396  405
0088 MASK       219   416  419  496  625  636  643  655
0006 MOTORPRT   207   267  286  340  416  416  419  419  496  496
                      636  636  643  643  655  655
0001 NDL1UL     187   325  337  362
FA22 NDL1UL5    472   577
0002 NDL5UL     188   309  346  353  356  359  379  510
```

| | | | | | | | | | |
|---|---|---|---|---|---|---|---|---|---|
| 0020 | NDLENB | 171 | 467 | 474 | | | | | |
| FA12 | NDLHOME | | 277 | 314 | 330 | 351 | 355 | 358 | 361 | 367 | 384 |
| | | 463 | 507 | 568 | | | | | |
| FAE6 | NDLLOC | | 310 | 326 | 338 | 347 | 354 | 357 | 360 | 363 | 380 |
| | | 556 | 511 | | | | | | |
| 0010 | NDLMOTN | 175 | 475 | | | | | | |
| 0020 | NDLMOTP | 172 | 468 | | | | | | |
| 00CF | NDLMSK | 177 | 471 | 478 | | | | | |
| 008A | NDLPOS | 221 | 463 | 557 | 560 | 569 | | | |
| 0004 | NDLSW1 | 173 | 469 | 561 | 570 | | | | |
| 0020 | NDLSW2 | 176 | 476 | 564 | 573 | | | | |
| 0010 | NDLTBRK | 174 | 470 | 477 | | | | | |
| 000C | OCRLSB | 78 | 584 | 586 | | | | | |
| 000B | OCRMSB | 77 | 587 | 589 | | | | | |
| 00FF | OFFSW | 208 | 290 | 644 | | | | | |
| 0000 | P1DDR | 9 | 263 | | | | | | |
| 0001 | P2DDR | 10 | 257 | | | | | | |
| 0004 | P3DDR | 32 | 265 | | | | | | |
| 000F | P3SREG | 87 | | | | | | | |
| 0005 | P4DDR | 33 | | | | | | | |
| 0006 | PLATE | 186 | 365 | | | | | | |
| 0002 | PORT1 | 12 | 197 | | | | | | |
| 0003 | PORT2 | 24 | | | | | | | |
| 0006 | PORT3 | 35 | 207 | | | | | | |
| 0007 | PORT4 | 48 | 206 | | | | | | |
| 0014 | RAMROM | 131 | | | | | | | |
| 0012 | RCVREG | 124 | | | | | | | |
| 0010 | RMCREG | 102 | | | | | | | |
| 0004 | SAMPWELL | 184 | 322 | 334 | | | | | |
| FAA8 | SOAK | 526 | 369 | | | | | | |
| 00AF | SOAKTIME | 209 | 526 | | | | | | |
| 00FF | STACK | 194 | 271 | 305 | | | | | |
| 008B | STATUS | 222 | 254 | 281 | 297 | 303 | | | |
| 000F | SWBOUNCE | 198 | 479 | | | | | | |
| 0086 | SWITCH | 217 | 621 | 633 | 637 | 645 | 650 | 669 | |
| 0007 | SWPRT | 206 | 291 | 486 | 504 | 540 | 543 | 549 | 552 | 562 | 565 |
| | | 571 | 574 | 634 | 638 | 646 | 651 | 670 | |
| 0087 | TBRAKE | 218 | 419 | 496 | 623 | 655 | 684 | | |
| 0008 | TCSREG | 63 | 259 | 491 | 492 | 497 | 499 | 527 | 579 | 583 | 592 |
| | | 594 | 627 | 628 | 630 | 656 | 658 | 660 | 661 | 677 |
| 1FFF | TONE | 205 | 578 | | | | | | |
| 02FF | TONE1 | 200 | 598 | | | | | | |
| 04FF | TONE2 | 201 | 602 | | | | | | |
| 08FF | TONE3 | 202 | 606 | | | | | | |
| 0FFF | TONE4 | 203 | 610 | | | | | | |
| 1FFF | TONE5 | 204 | 612 | | | | | | |
| 0081 | TONES | 213 | 513 | 524 | | | | | |
| 0040 | TRAY | 180 | 503 | | | | | | |
| FA73 | TRAYIN | 503 | 614 | | | | | | |
| 0011 | TRCSRG | 113 | | | | | | | |
| F9D6 | TUBEDOWN | | 308 | 315 | 319 | 324 | 331 | 336 | 345 | 352 | 368 |
| | | 429 | 373 | 378 | 385 | 407 | | | |
| 0040 | TUBEENB | 155 | 424 | 432 | | | | | |
| F9C9 | TUBEHOME | | 275 | 311 | 316 | 321 | 327 | 333 | 339 | 348 | 364 |
| | | 421 | 370 | 375 | 381 | 386 | 409 | 508 | |
| 0004 | TUBEMOTN | 159 | 433 | | | | | | |
| 0008 | TUBEMOTP | 156 | 425 | | | | | | |
| 00F3 | TUBEMSK | 161 | 428 | 436 | | | | | |
| 0002 | TUBESW1 | 157 | 426 | 485 | | | | | |
| 0010 | TUBESW2 | 160 | 434 | | | | | | |
| 0004 | TUBETBRK | 158 | 427 | 435 | | | | | |
| FA44 | UPDATIME | 491 | 694 | | | | | | |
| 0001 | WASH | 181 | 306 | 343 | 376 | | | | |
| 0080 | WASHTIMS | 212 | 279 | 387 | 410 | 412 | | | |
| 0002 | WASTE | 182 | 312 | 382 | | | | | |
| 0083 | WATCHDOG | 214 | 493 | 631 | 659 | 664 | 665 | 668 | |
| 0013 | XMTREG | 125 | | | | | | | |

What is claimed is:

1. Automatic pipetting apparatus comprising
a base,
sample plate means disposed on said base, said sample plate means having longitudinal and lateral dimensions, said plate means including a lateral row of liquid sample chambers and a lateral application space longitudinally separated from said liquid chamber row, said lateral application space adapted to receive a microporous support medium, said sample chambers adapted to receive liquid samples,
a pipette frame including vertical support means for supporting said frame from said base laterally above said sample plate means, said pipette frame having a longitudinal position with respect to said longitudinal dimension of said sample plate means,
longitudinal translation means for changing the longitudinal position between said pipette frame and said sample plate means,
a mounting plate carried by said pipette frame,
vertical translation means for effecting relative vertical movement of said mounting plate and said sample plate means,
a plurality of microsyringe barrels having their heads secured in a row to said mounting plate, said barrels spaced corresponding to the spacing of said liquid chambers on said plate, said barrels being hollow with each having a lower tip,
a plurality of micro-plungers, each of said plungers disposed in one of said barrels,
plunger translation means for moving said plungers vertically within said barrels,
signalling means
for generating longitudinal signals representative of the relative longitudinal orientation of said pipette frame with respect to said sample plate means,
for generating mounting plate signals representative of the vertical orientation of said mounting plate relative to said sample plate means and
for generating plunger signals representative of the orientation of said plungers relative to said barrels, and
programmed computer means responsive to said longitudinal signals, to said mounting plate signals and to said plunger signals for generating a sequence of control signals to said longitudinal translation means, to said vertical translation means and to said plunger translation means to aspirate a first predetermined amount of liquid from said sample chambers into said respective pipette barrels, and to apply a droplet of said liquid samples in each of said pipette barrels onto corresponding spaces of said microporous support medium when placed on said lateral application space of said sample plate by precisely positioning said lower tips of said barrels at a small distance above said microporous support medium, said small distance being smaller than the diameter of a droplet of liquid sample which may be maintained on the end of said tips through surface tension forces of the barrel tips, whereby each droplet slightly touches said microporous support medium and is thereby relieved of its surface tension and is precisely transferred to said microporous support medium from each of said pipette barrels.

2. The apparatus of claim 1 wherein
said sample plate means is translated longitudinally beneath said pipette frame by said longitudinal translation means.

3. The apparatus of claim 1 wherein
said pipette frame is translated longitudinally above said sample plate means by said longitudinal translation means.

4. The apparatus of claim 1 wherein said sample plate means includes a wash well adapted to contain wash liquid and a waste well longitudinally spaced from each other and from said sample chambers,
said programmed computer means generating a further sequence of control signals to said longitudinal translation means, to said vertical translation means and to said plunger translation means before aspirating liquid from said sample chambers,
to draw a second predetermined amount of wash liquid from said wash well into respective pipette barrels, and
to discharge said wash liquid into said waste well.

5. The apparatus of claim 1 wherein said sample plate means further includes a wash well adapted to contain wash liquid and a waste well longitudinally spaced from each other and from said sample chambers and a row of individual liquid dilution wells longitudinally spaced from said sample chambers, said dilution wells adapted to receive dilution liquid,
said programmed computer means generating a further sequence of control signal to said longitudinal translation means, to said vertical translation means and to said plunger translation means after aspirating liquid samples of said liquid samples into said pipette barrels,
to aspirate a second predetermined amount of wash fluid from said wash well into said respective pipette barrels operably creating a combination of sample liquid and wash liquid in each barrel,
to discharge said sample liquid/wash liquid into said corresponding dilution wells operably creating diluted liquid samples, and
to aspirate a third predetermined amount of diluted liquid samples from said dilution wells into said respective pipette barrels.

6. The apparatus of claim 5 wherein
said programmed computer means generates a further sequence of control signals to said plunger translation means to alternatingly discharge said sample liquid/wash liquid into said corresponding dilution wells and aspirate a predetermined amount of diluted liquid from said dilution wells into said respective pipette barrels operatively causing mixing of said liquid samples with said dilution liquid in said dilution wells.

7. The apparatus of claim 4 wherein said sample plate means further includes a row of individual liquid dilution wells longitudinally spaced from said sample chambers, said dilution wells adapted to receive dilution liquid,
said programmed computer means generating a further sequence of control signals to said longitudinal translation means, to said vertical translation means and to said plunger translation means for applying said first predetermined amount of liquid sample in each barrel to said dilution wells, applying a third predetermined amount of wash liquid from each barrel to said dilution wells, mixing the combination of said wash liquid and said liquid sample of said dilution wells, and aspirating an amount of diluted liquid samples from said dilution wells into said respective pipette barrels.

8. Automatic pipetting apparatus comprising a base, sample plate means disposed on said base, said sample plate means having longitudinal and lateral dimensions, said plate means including a lateral row of liquid sample chambers and a lateral application space longitudinally separated from said liquid chamber row, said lateral application space adapted to receive a microporous support medium, said sample chambers adapted to receive liquid samples, a pipette frame including vertical support means for supporting said frame from said base laterally above said sample plate means, said pipette frame having a longitudinal position with respect to said longitudinal dimension of said sample plate means, longitudinal translation means for changing the relative longitudinal position between said pipette frame and said sample plate means, a mounting plate carried by said pipette frame, vertical translation means for effecting relative vertical movement of said mounting plate and said sample plate means, a plurality of microsyringe barrels having their heads secured in a row to said mounting plate, said barrels spaced corresponding to the spacing of said liquid chambers on said plate, said barrels being hollow with each having a lower tip, a plurality of micro-plungers, each of said plungers disposed in one of said barrels, plunger translation means for moving said plungers vertically within said barrels, signalling means
    for generating longitudinal signals representative of the relative longitudinal orientation of said pipette frame with respect to said sample plate means,
    for generating mounting plate signals representative of the vertical orientation of said mounting plate relative to said sample plate means and
    for generating plunger signals representative of the orientation of said plungers relative to said barrels, and programmed computer means responsive to said longitudinal signals, to said mounting plate signals and to said plunger signals for generating a sequence of control signals to said longitudinal translation means, to said vertical translation means and to said plunger translation means to aspirate a first predetermined amount of liquid from said sample chambers into said respective pipette barrels, and to apply said liquid samples in each of said pipette barrels, where said lower tips of said barrels are at a position slightly above said microporous support medium onto corresponding spaces of said microporous support medium when placed on said lateral application space of said sample plate, wherein said sample plate means includes a wash well adapted to contain wash liquid and a waste well longitudinally spaced from each other and from said sample chambers, said programmed computer means generating a further sequence of control signals to said longitudinal translation means, to said vertical translation means and to said plunger translation means before aspirating liquid from said sample chambers,
to draw a second predetermined amount of wash liquid from said wash well into respective pipette barrels, and
to discharge said wash liquid into said waste well, and wherein said sample plate means includes a longitudinal blotting space for applying a lateral blotting paper strip, said blotting space longitudinally separated from said sample chambers row, said wash well, said waste well and said lateral application space, and said programmed computer means generating a further sequence of control signals to said longitudinal translation means, to said vertical translation means and to said plunger translation means after discharging said rinse liquid into said waste well, to blot the tips of said barrels on said blotting paper strip.

9. A sample plate adapted for use with automatic pipetting apparatus comprising a lateral row of individual liquid sample chambers and a lateral application space longitudinally separated from said liquid chamber row, said lateral application space adapted to receive a microporous support medium and
    including a raised portion and a lower portion, said row of individual liquid sample chambers being disposed on said raised portion, said lateral application space being disposed on said lower portion and further comprising a wash well and a waste well longitudinally spaced from each other and from said sample chambers.

10. The sample plate of claim 9 further comprising a row of individual liquid dilution wells longitudinally spaced from said sample chambers.

11. A sample plate adapted for use with automatic pipetting apparatus comprising a lateral row of individual liquid sample chambers and a lateral application space longitudinally separated from said liquid chamber row, said lateral application space adapted to receive a microporous support medium, and
    further comprising a wash well and a waste well longitudinally spaced from each other and from sample chambers, and
    further including a longitudinal blotting space for applying a lateral blotting paper strip, said blotting space longitudinally separated from said sample chamber row, said wash well, said waste well and said lateral application space.

12. The sample plate of claim 11 including a raised portion and a lower portion, said row of individual liquid sample chambers being disposed on said raised portion, said lateral application space being disposed on said lower portion.

13. The sample plate of claim 11 including a raised portion and a lower portion, said row of individual liquid sample chambers, said wash well and said waste well being disposed on said raised portion, said lateral application space and said blotting space being disposed on said lower portion.

14. Automatic pipetting apparatus comprising,
a base,
track means disposed longitudinally on said base,
a carriage longitudinally movably disposed on said track means,
a sample plate removably disposed on said carriage, said sample plate including a lateral row of individual liquid sample chambers and a lateral application space longitudinally separated from said liquid chamber row, said lateral application space adapted to receive a microporous support medium, said sample chambers adapted to receive sample liquids,
a pipette frame mounted vertically on said base above said carriage and said sample plate, said pipette frame having vertical mounting posts separated longitudinally from each other, each of said posts secured to said base, a mounting plate assembly slidably guided by said posts and disposed laterally with respect to said sample plate and including, a mounting plate having slidable guides disposed about said posts, a barrel bar fixed to said mounting plate, a plurality of microsyringe barrels having their heads secured in a row in said barrel bar and spaced corresponding to the spacing of said liquid chambers on said plate, said barrels being hollow with each having a lower tip, a plunger bar vertically movably disposed above said barrel bar and having a plurality of microplungers secured thereto, each of said microplungers movably disposed within a corresponding microsyringe barrel, and a plunger actuator plate vertically movable with respect to said mounting plate and carried by said mounting plate, said actuator plate removably secured to said plunger bar, translation and signalling means for moving said carriage longitudinally forward beneath said mounting plate assembly and generating carriage position signals indicative of said carriage position, moving said mounting plate assembly vertically with respect to said base and generating mounting plate position signals indicative of mounting plate position, and moving said plunger actuator bar and said plunger bar vertically with respect to said mounting plate and generating plunger bar position signals indicative of plunger bar position, and programmed computer means responsive to said carriage position signals, to said mounting plate position signals and to said plunger bar position signals for generating a sequence of control signals to said translation means for translating said carriage, said mounting plate and said plunger bar to aspirate a first predetermined amount of liquid from said sample chambers into said respective pipette barrels, and to apply a droplet of said liquid samples in each of said pipette barrels onto corresponding spaces of said microporous support medium when placed on said lateral application space of said sample plate by precisely positioning said lower tips of said barrels at a small distance above said microporous support medium, said small distance being smaller than the diameter of a droplet of liquid sample which may be maintained on the end of said tips through surface tension forces of the barrel tips, whereby each droplet slightly touches said microporous support medium and is thereby relieved of its surface tension and is precisely transferred to said microporous support medium from each of said pipette barrels.

15. The apparatus of claim 14 wherein said sample plate includes a wash well and a waste well longitudinally spaced from each other and from said sample chambers, said programmed computer means generating a further sequence of control signals to said translation means before aspirating liquid from said sample chambers, to draw a second predetermined amount of rinse liquid from said wash well into respective pipette barrels, and to discharge said rinse liquid into said waste well.

16. The apparatus of claim 14 wherein said translation and signalling means comprises, carriage translation means responsive to carriage translative signals for longitudinally translating said carriage and said sample plate on said track means beneath said pipette assembly for operably translating said plate to at least a sample chamber position where said sample chambers are beneath said microsyringe barrels and to an application position where said microporous support medium is beneath said microsyringe barrels, carriage signalling means for generating a sample chamber carriage position signal when said sample chambers are beneath said microsyringe barrels, and an application position signal where said microporous support medium is beneath said microsyringe barrels, mounting plate assembly translating means responsive to up and down mounting plate assembly translation signals for vertically translating said mounting plate assembly between an upper position and a lower position, said upper position being sufficiently high to lift said microsyringe barrels above said plate operably allowing translation of said plate beneath said barrels, said lower position operably allowing insertion of said barrels into said fluid sample chambers when said plate is in said sample chamber position and operably allowing said barrels to be slightly above said microporous support medium when secured to said lateral application space of said plate, mounting plate signalling means for generating a mounting plate upper position signal when said mounting plate is in said upper position and a mounting plate lower position signal when said mounting plate is in said lower position, plunger actuator plate translating means responsive to up and down plunger actuator plate translation signals for vertically translating said plunger actuator plate and said plunger bar between a lower position where said micro-plungers are fully within said corresponding microsyringe barrels to a sample upper position where said micro-plungers are extended upwardly through said barrels operably drawing fluid into said barrels when said tips are immersed in fluid in said sample chamber, plunger actuator plate signalling means for generating a plunger bar lower position signal when said plunger actuator plate and said plunger bar are in said lower position, and a plunger bar sample upper position signal when said plunger actuator plate and said plunger bar are in said sample upper position, and electrical means for providing signal communication between said programmed digital computer and said carriage translation means, said mounting plate assembly translating means, and said plunger actuator plate translating means, and for providing signal communication between said digital computer and said carriage signalling means, said mounting plate signalling means, and said plunger actuator plate signalling means.

17. The apparatus of claim 16 wherein said digital computer means includes a stored sequence of instructions for generating and applying said carriage translation signal to said carriage translation means thereby translating said carriage to said sample chamber position and removing said carriage translation signal when said sample chamber carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, said programmed digital computer means operably generating and applying said up plunger actuator plate translation signal to said plunger actuator plate translating means thereby translating said plungers from said lower position to said sample upper position and removing said plunger actuator plate translation signal when said plunger bar sample upper position signal is received, operably causing fluid in each of said sample chambers to be aspirated into said corresponding barrels, said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received, said programmed digital computer means operably generating and applying said carriage translation signal to said carriage translation means thereby translating said carriage to said application position and removing said carriage translation signal when said application carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, and said programmed digital computer means operably generating and applying said down plunger actuator plate translation signal to said plunger actuator plate translating means thereby translating said plunger from said sample upper position to said lower position and removing said plunger actuator plate translation signal when said plunger bar sample lower position signal is received, operably causing fluid in each of said barrels to be applied to said microporous support medium when secured to said lateral application space of said plate.

18. The apparatus of claim 17 wherein
said sample plate further includes
a wash well and a waste well longitudinally spaced from each other and from said sample chambers, and
said plunger actuator plate translating means further includes a wash upper position, and
said plunger actuator plate signalling means further includes means for generating a plunger bar wash upper position signal when said plunger actuator plate and said plunger bar are in said wash upper position, said carriage translation means further includes a wash well position and a rinse well position, and said carriage signalling means further includes means for generating a wash well carriage position signal when said wash well is beneath said microsyringe barrels and a waste well carriage position signal when said waste well is beneath said microsyringe barrels, said digital computer means includes a further stored sequence of instructions for before aspirating liquid from said sample chambers, generating and applying said carriage translation signal to said carriage translation means thereby translating said carriage to said wash well position and removing said carriage translation signal when said wash well carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, said programmed digital computer means operably generating and applying said up plunger actuator plate translation signal to said plunger actuator plate translating means thereby translating said plungers from said lower position to said wash upper position and removing said plunger actuator plate translation signal when said plunger bar wash upper position signal is received, operably causing fluid in said wash well to be aspirated into said barrels, said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received, said programmed digital computer means operably generating and applying said carriage translation signal to said carriage translation means thereby translating said carriage to said wash well position and removing said carriage translation signal when said wash well carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, said programmed digital computer means operably generating and applying said down plunger actuator plate translation signal to said plunger actuator plate translating means thereby translating said plunger from said wash upper position to said lower position and removing said plunger actuator plate translation signal when said plunger bar lower position signal is received, operably causing fluid in each of said barrels to be applied to said waste well, and said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received.

19. The apparatus of claim 14 wherein said means for translating said carriage longitudinally forward and backward beneath said mounting plate assembly comprises a carriage actuating motor fixed to said base, said motor having a rotatable output shaft, a pinion gear fixed to said output shaft, a rack gear secured to said carriage, said rack gear being in engagement with said pinion gear whereby the output shaft turning of said motor translates said carriage.

20. The apparatus of claim 14 wherein said means for translating said mounting plate assembly up and down with respect to said base comprises a mounting plate actuator motor fixed to said mounting plate, said motor having a rotatable output shaft, pinion gear means fixed to said output shaft, a rack gear secured to said base, said rack gear being in engagement with said pinion gear means whereby the output shaft turning of said mounting plate actuator motor translates said mounting plate up or down with respect to said base.

21. The apparatus of claim 14 wherein said signalling means for generating mounting plate position signals indicative of mounting plate position includes upper stop means secured to a member secured to said base, upper trip switch means secured to said mounting plate and having a trip arm for engaging said upper stop means for operatively tripping said upper trip switch means when said mounting plate reaches its upper limit of travel, lower stop means secured to said base, and lower trip switch means secured to said mounting plate having a trip arm for engaging said lower stop means for operatively tripping said lower trip switch means when said mounting plate reaches its lower limit of travel.

22. The apparatus of claim 14 wherein said sample plate means further includes a row of individual liquid dilution wells longitudinally spaced from said sample chambers, said diluted wells adapted to receive dilution liquid, said programmed computer means generating a further sequence of control signals to said longitudinal translation means, to said vertical translation means and to said translation signalling means for moving said plunger actuator bar and said plunger bar vertically with respect to said mounting plate for applying said first predetermined amount of liquid sample in each barrel to said dilution wells, applying a third predetermined amount of wash liquid from each barrel to said dilution wells, mixing the combination of said wash liquid and said liquid sample of said dilution wells, and aspirating an amount of diluted liquid samples from said dilution wells into said respective pipette barrels.

23. Automatic pipetting apparatus comprising, a base, track means disposed longitudinally on said base, a carriage longitudinally movably disposed on said track means, a sample plate removably disposed on said carriage, said sample plate including a lateral row of individual liquid sample chambers and a lateral application space longitudinally separated from said liquid chamber row, said lateral application space adapted to receive a microporous support medium, said sample chambers adapted to receive sample liquids, a pipette frame mounted vertically on said base above said carriage and said sample plate, said pipette frame having vertical mounting posts separated longitudinally from each other, each of said posts secured to said base, a mounting plate assembly slidably guided by said posts and disposed laterally with respect to said sample plate and including, a mounting plate having slidable guides disposed about said posts, a barrel bar fixed to said mounting plate, a plurality of microsyringe barrels having their heads secured in a row of said barrel bar and spaced corresponding to the spacing of said liquid chambers on said plate, said barrels being hollow with each having a lower tip, a plunger bar vertically movably disposed above said barrel bar and having a plurality of microplungers secured thereto, each of said microplungers movably disposed within a corresponding barrel of said microsyringes, and a plunger actuator plate vertically movable with respect to said mounting plate and carried by said mounting plate, said actuator plate removably secured to said plunger bar, translation and signalling means for moving said carriage longitudinally forward beneath said mounting plate assembly and generating carriage position signals indicative of said carriage position, moving said mounting plate assembly vertically with respect to said base and generating mounting plate position signals indicative of mounting plate position, and moving said plunger actuator bar and said plunger bar vertically with respect to said mounting plate and generating plunger bar position signals indicative of plunger bar position, and programmed computer means responsive to said carriage position signals, to said mounting plate position signals and to said plunger bar position signals for generating a sequence of control signals to said translation means for translating said carriage, said mounting plate and said plunger bar to aspirate a first predetermined amount of liquid from said sample chambers into said respective pipette barrels, and to apply said liquid in each of said pipette barrels from a position slightly above said microporous support medium whereby droplets of said liquid which forms on the tops of said barrels are transferred from said tips onto corresponding spaces of said microporous support medium when placed on said lateral application space of said sample plate, and wherein said sample plate includes a wash well and a waste well longitudinally spaced from each other and from said sample chambers, said programmed computer means generating a further sequence of control signals to said translation means before aspirating liquid from said sample chambers, to draw a second predetermined amount of rinse liquid from said wash well into respective pipette barrels, and to discharge said rinse liquid into said waste well and wherein said sample plane includes a longitudinal blotting space for applying a lateral blotting paper strip, said blotting space longitudinally separated from said sample chamber row, said wash well, said waste well and said lateral application space, and said programmed computer means generating a further sequence of control signals to said translation means after discharging said rinse liquid into said waste well, to blot the tips of said barrels on said blotting paper strip.

24. The apparatus of claim 23 wherein said sample plate includes a raised portion and a lower portion, said row of individual liquid sample chambers, said wash well and said waste well being disposed on said raised portion, said lateral application space and said blotting space being disposed on said lower portion.

25. The apparatus of claim 23 wherein said sample plate includes a raised portion and a lower portion, said row of individual liquid sample chambers being disposed on said raised portion, said lateral application space being disposed on said lower portion.

26. The apparatus of claim 25 wherein said signalling means for generating carriage position signals indicative of carriage position includes said carriage having a first longitudinal surface with notches disposed thereon, the longitudinal separation of said notches corresponding to the longitudinal position of said wash well, said waste well, said longitudinal blotting space, said sample chambers and said lateral application space, a first trip switch secured to said track means on which said carriage moves, said switch having a first spring forced roller means for engaging said longitudinal surface whereby said switch is tripped when said roller is forced into a notch, operatively indicating that said wash well or said waste well or said longitudinal blotting space, or said sample chambers, or said lateral application space is beneath said microsyringe barrels.

27. The apparatus of claim 26 wherein said signalling means for generating carriage position signals indicative of carriage position includes said carriage having a second longitudinal surface with at least one notch disposed thereon near the forward end of said carriage, a second trip switch secured to said track on which said carriage moves, said second switch having a second spring forced roller means for engaging said second longitudinal surface whereby said switch is tripped when said second roller means is forced into said notch operatively indicating that said carriage has reached its rearward limit of travel.

28. The apparatus of claim 27 further comprising a limit switch means secured to the rear of said carriage at a position for engaging the forward end of said plate for indicating that said plate is in an operative position within said carriage.

29. The apparatus of claim 25 wherein said means for translating said plunger bar up and down with respect to said mounting plate comprises a plunger plate motor fixed to said mounting plate, said motor having a rotatable output shaft, pinion gear means fixed to said output shaft, rack gear means fixed to said plunger actuator plate, said rack gear being in engagement with said pinion gear means whereby the output shaft turning of said plunger actuator plate motor translates said actuator plate and said plunger bar up or down with respect to said mounting plate.

30. The apparatus of claim 29 wherein said plunger actuator plate motor is fixed to the rear side of said mounting plate, said mounting plate includes two vertically plunger actuator plate guides with vertical grooves provided therein, said guides being fixed to the forward side of said mounting plate, said plunger actuator plate is slidingly disposed within said vertical grooves on said mounting plate, said mounting plate has vertical slots therein, and said rack gear means fixed to said plunger actuator plate extend from said plunger actuator plate on the forward side of said mounting plate to said pinion gear means fixed to said output shaft of said plunger actuator plate motor on the rear side of said mounting plate.

31. The apparatus of claim 29 wherein said signalling means for generating plunger bar position signals indicative of plunger bar position includes application cam means vertically adjustable on a vertical shaft secured to said plunger actuator plate, wash cam means vertically adjustable on a vertical shaft secured to said plunger actuator plate, a first trip switch means secured to said mounting plate and having a trip arm for engaging said application cam means for operatively tripping said first trip switch means when said plunger actuator plate reaches an upper application position, and operatively tripping said first trip switch means when said plunger actuator plate reaches an upper wash position, lower cam means vertically adjustable on a vertical shaft secured to said plunger actuator plate, and a second trip switch means secured to said mounting plate and having a trip arm for engaging said down cam means for operatively tripping said second trip means when said plunger actuator plate reaches its lower limit of travel.

32. Automatic pipetting apparatus comprising, a base, track means disposed longitudinally on said base, a carriage longitudinally movably disposed on said track means, a sample plate removably disposed on said carriage, said sample plate including a lateral row of individual liquid sample chambers and a lateral application space longitudinally separated from said liquid chamber row, said lateral application space adapted to receive a microporous support medium, said sample chambers adapted to receive sample liquids, a pipette frame mounted vertically on said base above said carriage and said sample plate, said pipette frame having vertical mounting posts separated longitudinally from each other, each of said posts secured to said base, a mounting plate assembly slidably guided by said posts and disposed laterally with respect to said sample plate and including,
- a mounting plate having slidable guides disposed about said posts,
- a barrel bar fixed to said mounting plate,
- a plurality of microsyringe barrels having their heads secured in a row in said barrel bar and spaced corresponding to the spacing of said liquid chambers on said plate, said barrels being hollow with each having a lower tip,
- a plunger bar vertically movably disposed above said barrel bar and having a plurality of microplungers secured thereto, each of said microplungers movably disposed within a corresponding barrel of said microsyringes, and
- a plunger actuator plate vertically movable with respect to said mounting plate and carried by said mounting plate, said actuator plate removably secured to said plunger bar, translation and signalling means for
- moving said carriage longitudinally forward beneath said mounting plate assembly and generating carriage position signals indicative of said carriage position,
- moving said mounting plate assembly vertically with respect to said base and generating mounting plate position signals indicative of mounting plate position, and
- moving said plunger actuator bar and said plunger bar vertically with respect to said mounting plate and generating plunger bar position signals indicative of plunger bar position, and programmed computer means responsive to said carriage position signals, to said mounting plate position signals and to said plunger bar position signals for generating a sequence of control signals to said translation means for translating said carriage, said mounting plate and said plunger bar to aspirate a first predetermined amount of liquid from said sample chambers into said respective pipette barrels, and to apply said liquid in each of said pipette barrels from a position slightly above said microporous support medium whereby droplets of said liquid which forms on the tops of said barrels are transferred from said tips onto corresponding spaces of said microporous support medium when placed on said lateral application space of said sample plate, wherein said translation and signalling means comprises, carriage translation means responsive to carriage translative signals for longitudinally translating said carriage and said sample plate on said track means beneath said pipette assembly for operably translating said plate to at least a sample chamber position where said sample chambers are beneath said microsyringe barrels and to an application position where said microporous support medium is beneath said microsyringe barrels, carriage signalling means for generating a sample chamber carriage position signal when said sample chambers are beneath said microsyringe barrels, and an application position signal where said microporous support medium is beneath said microsyringe barrels, mounting plate assembly translating means responsive to up and down mounting plate assembly translation signals for vertically translating said mounting plate assembly between an upper position and a lower position, said upper position being sufficiently high to lift said microsyringe barrels above said plate operably allowing translation of said plate beneath said barrels, said lower position operably allowing insertion of said barrels into said fluid sample chambers when said plate is in said sample chamber position and operably allowing said barrels to be slightly above said microporous support medium when secured to said lateral application space of said plate, mounting plate signalling means for generating a mounting plate upper position signal when said mounting plate is in said upper position and a mounting plate lower position signal when said mounting plate is in said lower position, plunger actuator plate translating means responsive to up and down plunger actuator plate translation signals for vertically translating said plunger actuator plate and said plunger bar between a lower position where said micro-plungers are fully within said corresponding microsyringe barrels to a sample upper position where said micro-plungers are extended upwardly through said barrels operably drawing fluid into said barrels when said tips are immersed in fluid in said sample chamber, plunger actuator plate signalling means for generating a plunger bar lower position signal when said plunger actuator plate and said plunger bar are in said lower position, and a plunger bar sample upper position signal when said plunger actuator plate and said plunger bar are in said sample upper position, and electrical means for providing signal communication between said programmed digital computer and said carriage translation means, said mounting plate assembly translating means, and said plunger actuator plate translating means, and for providing signal communication between said digital computer and said carriage signalling means, said mounting plate signalling means, and said plunger actuator plate signalling means, wherein said digital computer means includes a stored sequence of instructions for generating and applying said carriage translation signal to said carriage translation means thereby translating said carriage to said sample chamber position and removing said carriage translation signal when said sample chamber carriage position signal is received, said programmed digital computer means operably generating and applying said down mounting plate assembly translation signal to said mounting plate assembly translating means thereby translating said mounting plate assembly from said upper position and said lower position and removing said mounting plate assembly translation signal when said mounting plate lower position signal is received, said programmed digital computer means operably generating and applying said up plunger actuator plate translation signal to said plunger actuator plate translating means thereby translating said plungers from said lower position to said sample upper position and removing said plunger actuator plate translation signal when said plunger bar sample upper position signal is received, operably causing fluid in each of said sample chambers to be aspirated into said corresponding barrels, said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received, said programmed digital computer means operably generating and applying said carriage translation signal to said carriage translation means thereby translating said carriage to said application position and removing said carriage translation signal when said application carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, and said programmed digital computer means operably generating and applying said down plunger actuator plate translation signal to said plunger actuator plate translating means thereby translating said plunger from said sample upper position to said lower position and removing said plunger actuator plate translation signal when said plunger bar sample lower position signal is received, operably causing fluid in each of said barrels to be applied to said microporous support medium when secured to said lateral application space of said plate, wherein said sample plate further includes a wash well and a waste well longitudinally spaced from each other and from said sample chambers, and said plunger actuator plate translating means further includes a wash upper position, and said plunger actuator plate signalling means further includes means for generating a plunger bar wash upper position signal when said plunger actuator plate and said plunger bar are in said wash upper position, said carriage translation means further includes a wash well position and a rinse well position, and said carriage signalling means further includes means for generating a wash well carriage position signal when said wash well is beneath said microsyringe barrels and a waste well carriage position signal when said waste well is beneath said microsyringe barrels, said digital computer means includes a further stored sequence of instructions for before aspirating liquid from said sample chambers, generating and applying said carriage translation signal to said carriage translation means thereby translating said carriage to said wash well position and removing said carriage translation signal when said wash well carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, said programmed digital computer means operably generating and applying said up plunger actuator plate translation signal to said plunger actuator plate translating means thereby translating said plungers from said lower position to said wash upper position and removing said plunger actuator plate translation signal when said plunger bar wash upper position signal is received, operably causing fluid in said wash well to be aspirated into said barrels, said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received, said programmed digital computer means operably generating and applying said carriage translation signal to said carriage translation means thereby translating said carriage to said wash well position and removing said carriage translation signal when said wash well carriage position signal is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, said programmed digital computer means operably generating and applying said down plunger actuator plate translation signal to said plunger actuator plate translating means thereby translating said plunger from said wash upper position to said lower position and removing said plunger actuator plate translation signal when said plunger bar lower position signal is received, operably causing fluid in each of said barrels to be applied to said waste well, and said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received, and wherein said sample plate further includes a blotting space for applying a lateral blotting paper strip, said blotting space longitudinally separated from said sample chamber row, said wash well, said waste well and said lateral application space, said carriage translation means further includes a blotting position, and said carriage signalling means further includes means for generating a blotting carriage position signal when said blotting space is beneath said microsyringe barrels, said digital computer means includes a further stored sequence of instructions for after discharging said rinse liquid to said waste well, generating and applying said carriage translation signal to said carriage translation means thereby translating said carriage to said blotting position and removing said carriage translation signal when said blotting carriage position is received, said programmed digital computer means operably generating and applying said down mounting plate assembly translation signal to said mounting plate assembly translating means thereby translating said mounting plate assembly from said upper position to said lower position and removing said mounting plate assembly translation signal when said mounting plate lower position signal is received, whereby said barrel tips are blotted when said blotting paper is disposed on said blotting space, and said digital computer means includes a further stored sequence of instructions for said programmed digital computer means operably generating and applying said up mounting plate assembly translation signal to said mounting plate assembly translating means thereby translating said mounting plate assembly from said lower position to said upper position and removing said mounting plate assembly translation signal when said mounting plate upper position signal is received.

* * * * *